United States Patent
Quarta et al.

(10) Patent No.: US 11,628,188 B2
(45) Date of Patent: *Apr. 18, 2023

(54) METHODS AND COMPOSITIONS TO MAINTAIN STEM CELL QUIESCENCE

(71) Applicant: The Board of Trustees of the Leland Stanford Junior University, Stanford, CA (US)

(72) Inventors: Marco Quarta, Palo Alto, CA (US); Thomas A. Rando, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 368 days.

This patent is subject to a terminal disclaimer.

(21) Appl. No.: 16/870,486

(22) Filed: May 8, 2020

(65) Prior Publication Data
US 2020/0268804 A1 Aug. 27, 2020

Related U.S. Application Data

(63) Continuation of application No. 15/600,270, filed on May 19, 2017, now Pat. No. 10,688,136.

(60) Provisional application No. 62/339,531, filed on May 20, 2016.

(51) Int. Cl.
*A61K 35/34* (2015.01)
*C12N 5/077* (2010.01)

(52) U.S. Cl.
CPC ............ *A61K 35/34* (2013.01); *C12N 5/0658* (2013.01); *C12N 2500/25* (2013.01); *C12N 2500/90* (2013.01); *C12N 2501/15* (2013.01); *C12N 2501/34* (2013.01); *C12N 2501/999* (2013.01); *C12N 2510/00* (2013.01)

(58) Field of Classification Search
CPC ............... A61K 35/34; C12N 2500/25; C12N 2500/90; C12N 2501/15; C12N 2501/34; C12N 2501/999; C12N 2510/00; C12N 5/0658
See application file for complete search history.

(56) References Cited

U.S. PATENT DOCUMENTS 10,688,136 B2 * 6/2020 Quarta .................. A61K 35/34

OTHER PUBLICATIONS

Li et al., "Coexistence of quiescent and active adult stem cells in mammals", Science, Jan. 29, 2010. Pates 542-545, vol. 327, Issue 5965, AAAS, Washington, D.C.
Fuchs, "The tortoise and the hair: slow-cycling cells in the stem cell race", Cell, May 29, 2009, pp. 811-819, vol. 137, Issue 5, Isevier Inc., Amsterdam, Netherlands.
Cornelison et al., "Syndecan-3 and syndecan-4 specifically mark skeletal muscle satellite cells and are implicated in satellite cell maintenance and muscle regeneration", Dev Biol., Nov. 1, 2001, pp. 79-94, vol. 239, Issue 1, Academic Press, Cambridge, MA.
Fukada et al., "Purification and cell-surface marker characterization of quiescent satellite cells from murine skeletal muscle by a novel monoclonal antibody", Exp Cell Res., Jun. 10, 2004, pp. 245-255, vol. 296, Issue 2, Elsevier Inc., Amsterdam, Netherlands.
Montarras et al., "Direct isolation of satellite cells for skeletal muscle regeneration", Science, Sep. 23, 2005, pp. 2064-2067, vol. 309, Issue 5743, AAAS, Washington, D.C.
Kuang et al., "Asymmetric Self-Renewal and Commitment of Satellite Stem Cells in Muscle", Cell, Jun. 1, 2007, pp. 999-1010, vol. 129, Issue 5, Elsevier Inc., Amsterdam, Netherlands.
Cerletti et al., "Highly efficient, functional engraftment of skeletal muscle stem ceils in dystrophic muscles", Cell, Jul. 11, 2008, pp. 37-47, vol. 134, Issue 1, Elsevier Inc., Amsterdam, Netherlands.
Collins et al., "Stem cell function, self-renewal, and behavioral heterogeneity of cells from the adult muscle satellite cell niche", Cell, Jul. 29, 2005, pp. 289-301, vol. 122, Issue 2, Elsevier Inc., Amsterdam, Netherlands.
Sacco et al., "Self-renewal and expansion of single transplanted muscle stem cells", Nature, Nov. 27, 2008, pp. 502-506, 456(7221), Macmillan Publishers Limited, Basingstoke, United Kingdom.
Sherwood et al., "Isolation of adult mouse myogenic progenitors: functional heterogeneity of cells within and engrafting skeletal muscle", Cell, Nov. 12, 2004, pp. 543-554, vol. 119, Cell Press, Cambridge, MA.
Sampaolesi et al., "Cell therapy of α-sarcoglycan null dystrophic mice through intra-arterial delivery of mesoangioblasts", Science, Jul. 25, 2003, pp. 487-492; vol. 301, Issue 5632, AAAS, Washington, D.C.

* cited by examiner

*Primary Examiner* — Blaine Lankford
(74) *Attorney, Agent, or Firm* — Pamela J. Sherwood; Bozicevic, Field & Francis LLP

(57) ABSTRACT

Compositions and methods are provided for induction and maintenance of quiescence of stem cells.

19 Claims, 17 Drawing Sheets

FIG 2A.
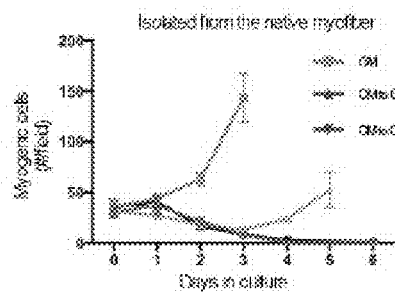 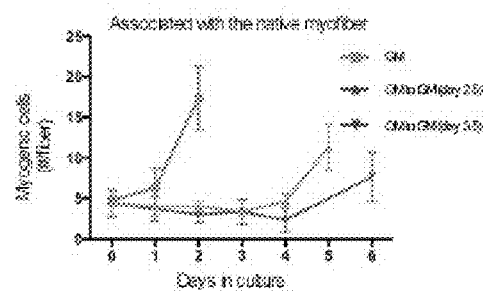

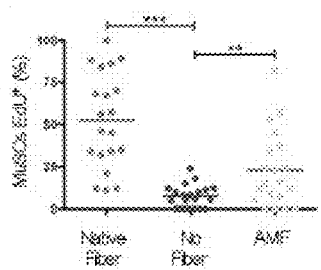 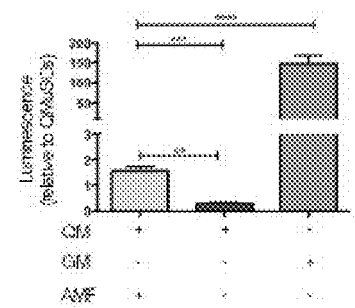 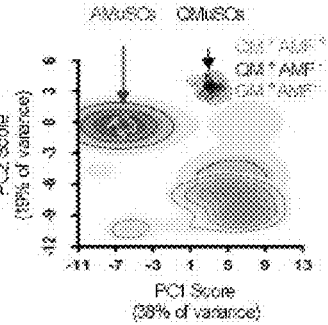
FIG. 2F     FIG. 2G     FIG. 2H

FIG. 3A
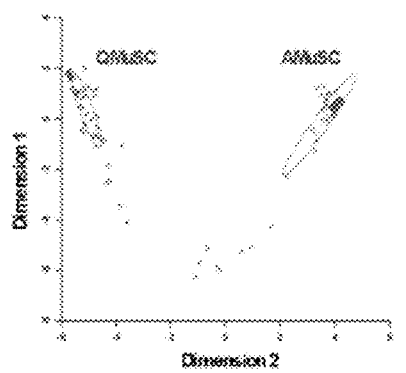
FIG. 3B
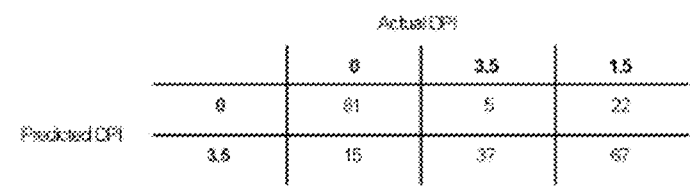
FIG. 3C
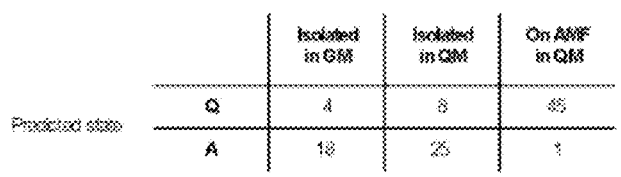
FIG. 3D
FIG. 3E
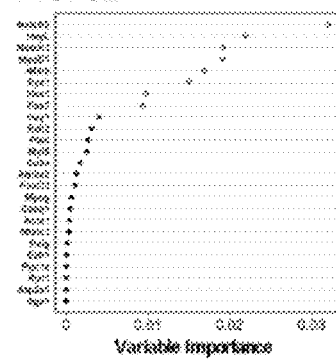
FIG. 3F
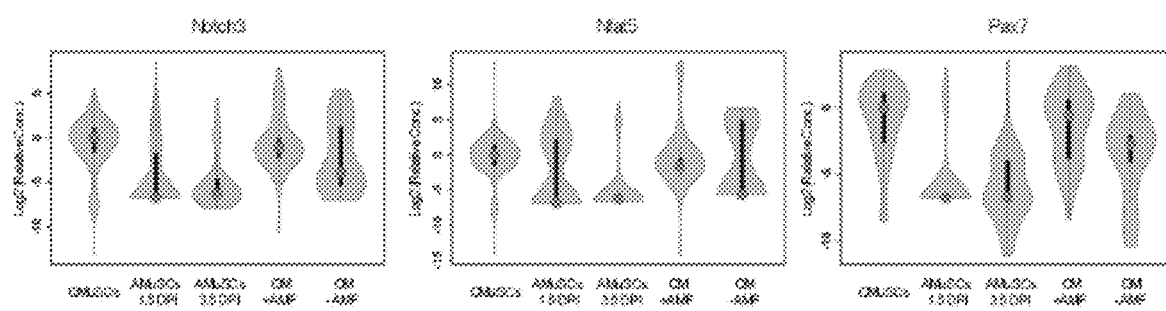

FIG. 4A
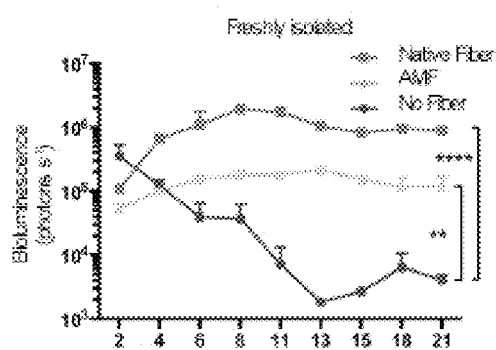
FIG. 4B
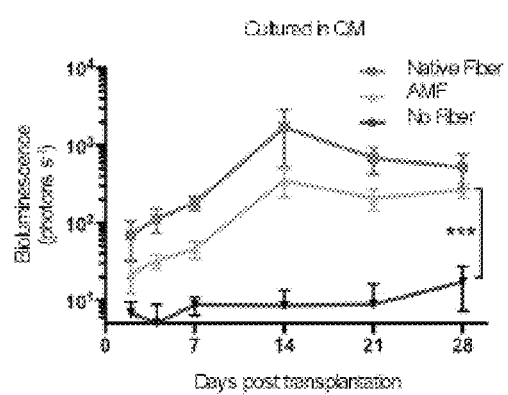
FIG. 4C
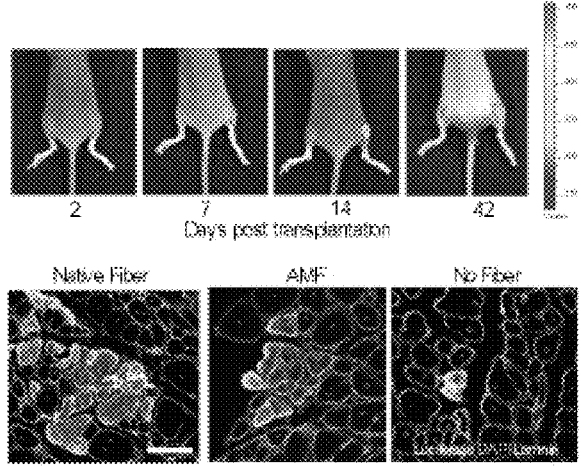
FIG. 4E
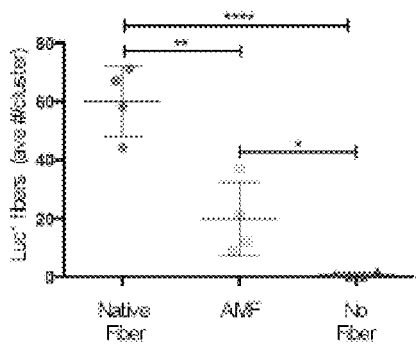
FIG. 4D

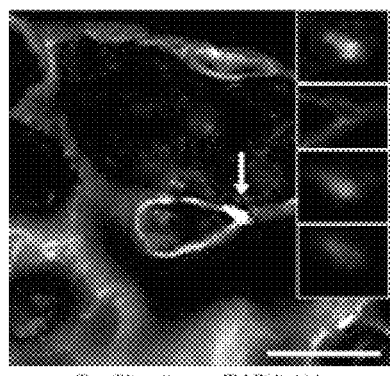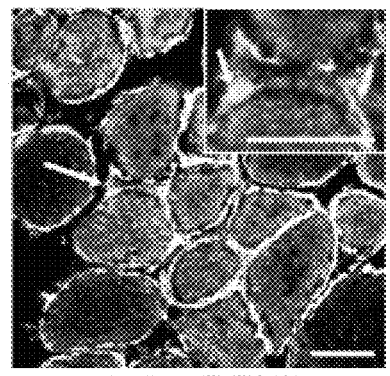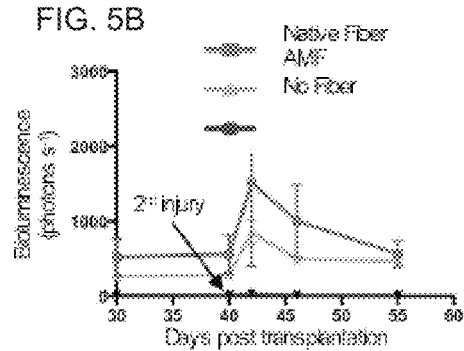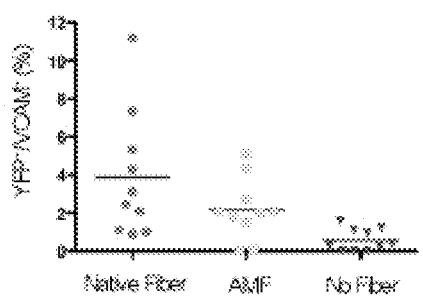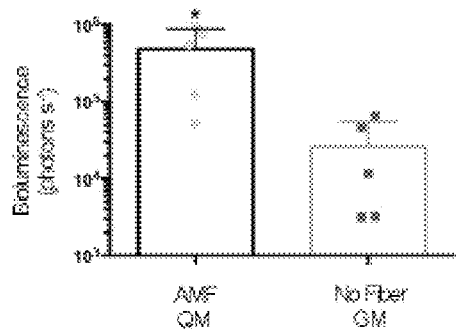
FIG. 5A
FIG. 5B
FIG. 5C
FIG. 5D FIG. 13A
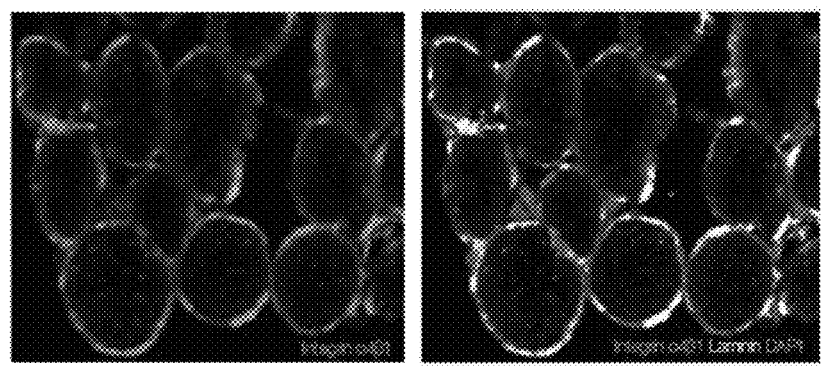
FIG. 13B
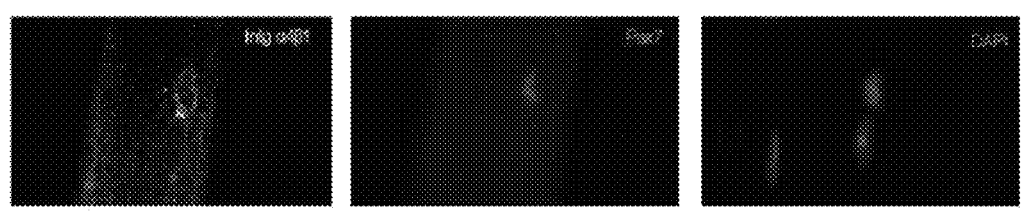
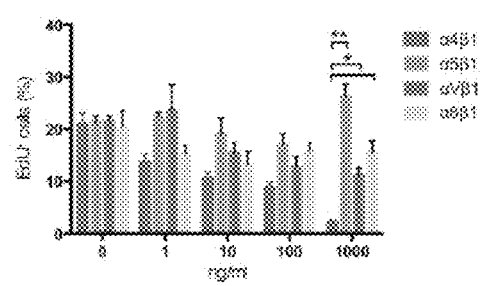
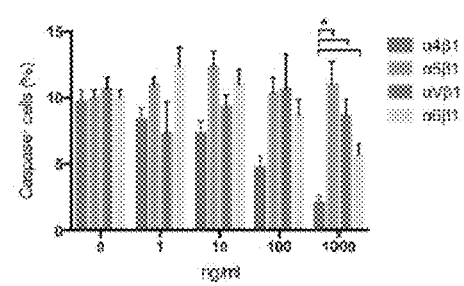
FIG. 13C     FIG. 13D

FIG. 16

| | |
|---|---|
| *Adapted from Hams F10 main formulation | |
| Component | g/L |
| Calcium Chloride | 0.0333 |
| Cupric Sulfate • 5H₂O | 0.0000025 |
| Ferrous Sulfate • 7H₂O | 0.000834 |
| Magnesium Sulfate (anhydrous) | 0.07464 |
| Potassium Chloride | 0.285 |
| Potassium Phosphate Monobasic (anhydrous) | 0.083 |
| Sodium Chloride | 7.4 |
| Sodium Phosphate Dibasic (anhydrous) | 0.1537 |
| Zinc Sulfate • 7H₂O | 0.0000288 |
| Amino Acids | |
| L-Alanine | 0.009 |
| L-Arginine • HCl | 0.211 |
| L-Asparagine • H₂O | 0.01501 |
| L-Aspartic Acid | 0.0133 |
| L-Cysteine • HCl • H₂O | 0.035 |
| L-Glutamic Acid | 0.0147 |
| L-Glutamine | 0.146 |
| Glycine | 0.00751 |
| L-Histidine • HCl • H₂O | 0.021 |
| L-Isoleucine | 0.0026 |
| L-Leucine | 0.0131 |
| L-Lysine • HCl | 0.0293 |
| L-Methionine | 0.00448 |
| L-Phenylalanine | 0.00496 |
| L-Proline | 0.0115 |
| L-Serine | 0.0105 |
| L-Threonine | 0.00357 |
| L-Tryptophan | 0.0006 |
| L-Tyrosine • 2Na • 2H₂O | 0.00261 |
| L-Valine | 0.0035 |
| Vitamins | |
| D-Biotin | 0.000024 |
| Choline Chloride | 0.000698 |
| Folic Acid | 0.00132 |
| *myo*-Inositol | 0.000541 |
| Niacinamide | 0.000615 |
| D-Pantothenic Acid (hemicalcium) | 0.000715 |
| Pyridoxine • HCl | 0.000206 |
| Riboflavin | 0.000376 |

FIG. 16 (Cont. 1)

| | |
|---|---|
| Thiamine • HCl | 0.001 |
| Vitamin B$_{12}$ | 0.00136 |
| Other | |
| D-Glucose | 1.1 |
| Hypoxanthine | 0.00408 |
| Phenol Red • Na | 0.0013 |
| Pyruvic Acid • Na | 0.11 |
| Thioctic Acid | 0.00021 |
| Thymidine | 0.00073 |
| Sodium Bicarbonate | 1.2 |

| Small Molecules and Growth Factors | concentration |
|---|---|
| Elcatonin ( CLTR activator) (Prospec) | 1 uM |
| MGCD-265 (Sellec Chem) | 500 nM |
| JNJ-7706621 (Sellec Chem) | 500 nM |
| Forskolin (LC Laboratories) | 10 uM |
| Somatostatin (Sigma) | 10 nM |
| SB203580 (Cell Signaling Technology) | 25 uM |
| SU5402 (Santa Cruz Biotechnologies) | 10 uM |
| TGFbeta (R&D System) | 5 nM |
| Knock Out SR (Life Techologies) | 0.1% |

| Others | |
|---|---|
| Pluronic F-68 | 2.33E-02 |
| Dextran Sulphate (64-76KD) | 1.5 nM |
| Penicillin/Streptomycin | 1% |
| Selenium | 5 ng/ml |

Adapted QM for human MuSCs

Basic culture medium was a 1:1 adapted mixture of DMEM:MCDB

| Small Molecules and Growth Factors | concentration |
|---|---|
| Elcatonin ( CLTR activator) (Prospec) | 1 uM |
| SB203580 (Cell Signaling Technology) | 20 uM |
| SU5402 (Santa Cruz Biotechnologies) | 1 uM |
| Forskolin (LC Laboratories) | 1 uM |
| TGFbeta (R&D System) | 5 nM |
| Knock Out SR (Life Techologies) | 1% |
| Iinsulin-transferrin-selenium (ITS, Invitrogen) | 1% |
| penicillin-streptomycin. | 1% |

METHODS AND COMPOSITIONS TO MAINTAIN STEM CELL QUIESCENCE

CROSS REFERENCE

This application claims benefit and is a Continuation of application Ser. No. 15/600,270, filed May 19, 2017, which claims benefit of U.S. Provisional Patent Application No. 62/339,531, filed May 20, 2016, which application is incorporated herein by reference in its entirety.

FEDERALLY SPONSORED RESEARCH AND DEVELOPMENT

This invention was made with Government support under contracts AG036695, AG023806, AR062185, and AG047820 awarded by the National Institutes of Health. The Government has certain rights in the invention.

BACKGROUND OF THE INVENTION

Among the key properties that distinguish adult mammalian stem cells from their more differentiated progeny is the ability of stem cells to remain in a quiescent state for prolonged periods of time (Li & Clevers, Science 327, 542-545 (2010)), (Fuchs, Cell 137, 811-819 (2009)). Quiescence is a common feature of stem cells characterized by reversible mitotic arrest and reduced metabolic activity that protects stem cells against endogenous stress caused by DNA replication and cellular respiration. Quiescence of stem cells is critical to ensure lifelong tissue maintenance and to protect the stem cell pool from premature exhaustion under conditions of various stresses. However, the molecular pathways for the maintenance of stem-cell quiescence remain elusive.

Stem cells have a capacity both for self-renewal and the generation of differentiated cell types, which provides the possibility for therapeutic regeneration of cells and tissues in the body. In addition to studying the important normal function of stem cells in the regeneration of tissues, researchers have further sought to exploit the potential of in situ and/or exogenous stem cells for the treatment of a variety of disorders. While early, embryonic stem cells have generated considerable interest, the stem cells resident in adult tissues also provide an important source of regenerative capacity.

These somatic, or adult, stem cells are undifferentiated cells that reside in differentiated tissues, and have the properties of both self-renewal and generation of differentiated cell types. The differentiated cell types may include all or some of the specialized cells in the tissue. For example, hematopoietic stem cells give rise to all hematopoietic lineages, but do not seem to give rise to stromal and other cells found in the bone marrow. Sources of somatic stem cells include bone marrow, blood, the cornea and the retina of the eye, brain, skeletal muscle, cartilage, bones, dental pulp, liver, skin, the lining of the gastrointestinal tract, and pancreas, and the like. Adult stem cells are usually quite sparse. Often they are difficult to identify, isolate, and purify. Often, somatic stem cells are quiescent until stimulated by the appropriate growth signals.

Muscle tissue in adult vertebrates regenerates from stem cells known as satellite cells. Satellite cells are distributed throughout muscle tissue and are mitotically quiescent in the absence of injury or disease, residing in an instructive, anatomically defined niche. The satellite cell niche constitutes a distinct membrane-enclosed compartment within the muscle fiber, containing a diversity of biochemical and biophysical signals that influence satellite cell function. In addition to satellite cells, cell types that contribute to muscle regeneration include mesangioblasts, bone marrow derived cells, muscle interstitial cells, mesenchymal stem cells, etc. See D. D. Cornelison et al. (2001) Dev Biol 239, 79; S. Fukada et al. (2004) Exp Cell Res 296, 245; D. Montarras et al. (2005) Science 309, 2064; S. Kuang et al. (2007) Cell 129, 999; M. Cerletti et al. (2008) Cell 134, 37; C. A. Collins et al. (2005) Cell 122, 289; A. Sacco et al. (2008) Nature 456, 502; R. I. Sherwood et al. (2004) Cell 119, 543; Sampaolesi et al. (2003) Science 301(5632):487-92; and Galvez et al. (2006) J Cell Biol. 174(2):231-43.

Satellite cells are the primary cells in muscle tissue required for the regeneration that occurs in response to injury or disease. In response to injury, SCs are activated and they proliferate and differentiate into myoblasts that undergo further differentiation and fusion to form muscle fibers.

One of the current limitations for stem cell therapeutics is the inability to manipulate stem cells in vitro after isolation without the loss of their potency. Emerging data suggest that stem cells potency depends on their capacity to remain in a quiescent state prior their activation induced by regenerative stimuli such as injury. For many stem cell populations, such as skeletal muscle stem cells (MuSCs), hematopoietic stem cells (HSCs), or neural stem cells (NSCs), the most potent cell in terms of transplantation efficacy and their ability to repair and repopulate the tissue is the long-term quiescent stem cell. It has been estimated that such cells can remain in the quiescent state for months in mice and years in humans. Physiologically, stem cells reside within the tissue in a specialized microenvironment or "niche", which is characterized by a unique combination of biophysical, biochemical and cellular properties that promote stem cell quiescence in several tissue compartments. Among the major hurdles, in the basic studies and translational applications of stem cell biology, is the ability to mimic the endogenous niche ex vivo.

To date, bioengineered niches have focused almost exclusively on those aspects that influence the dynamics of dividing cells, allowing studies of cell replication and cell fate determination. What has not been well modeled is the endogenous niche that promotes and maintains stem cell quiescence. The major challenge to create such culture conditions is the fact that as soon as quiescent cells are isolated from their in vivo niche and plated in conventional culture conditions, they immediately begin exiting quiescence, activating, and undergoing the processes of proliferation and differentiation. The ability to maintain stem cells in a quiescent state ex vivo would be a major advance for the study of the biology of the quiescent state. Even more importantly, from a translational perspective, the isolation and culturing of quiescent stem cells followed by transplantation should preserve cell potency.

To be able to maintain stem cells in a potent, quiescent state ex vivo while allowing, for example, genetic manipulation prior to transplantation, would greatly enhance their therapeutic potential. Specifically, given the high potency of these cells, this approach would abrogate the need for expansion of progenitors in vitro and focus attention instead on the ability of very few quiescent stem cells to replace vast amounts of tissues, as has been shown for MuSCs, HSCs and NSCs. MuSCs, or "satellite cells", reside in a quiescent state under the basal laminae of muscle fibers. The transplantation potency of freshly isolated adult MuSCs is rapidly lost when they undergo activation or proliferation in vitro.

SUMMARY OF THE INVENTION

Methods are provided for the induction and/or maintenance of stem cell quiescence, including without limitation muscle stem cells. The quiescent stem cells induced or maintained by the methods of the invention can be genetically manipulated, and provide for enhanced regeneration when transplanted into an individual. In some embodiments the cells are human cells; and may be, without limitation, human muscle stem cells.

In some embodiments of the invention a culture medium, which may be referred to herein as quiescence medium (QM), that induces or maintains quiescence of stem cells during in vitro culture is provided. For mouse cells the quiescence medium is a serum-free medium comprising one or more of elcatonin; MGCD-265, JNJ-7706621, Forskolin, Somatostatin, SB203580, SU5402, TGFbeta and serum replacement. For human cells the quiescence medium comprises one or more of Elcatonin, SB203580, SU5402, Forskolin, TGFbeta, Knock Out SR, and Insulin-transferrin-selenium (ITS, Invitrogen). In some embodiments the medium comprises two or more, three or more, four or more, five or more, six, or all of the stated components.

In some embodiments, quiescent cells are seeded into QM for culture, in order to maintain the quiescent phenotype over a period of time, e.g. to allow for genetic modification of the cells. In some embodiments blasts, e.g. proliferating progenitor or stem cells are seeded into QM for culture in order to induce a quiescent phenotype. The blast cells may be, without limitation, myoblasts. The blast cells may have been expanded in culture, or may have been isolated from an individual. Such cells may be referred to as induced quiescent cells. An advantage of inducing quiescence is an increase in transplantable cells, e.g. an increase of at least about 2-fold, at least about 3-fold, at least about 4-fold, at least about 5-fold, at least about 1-fold, at least about 20-fold, at least about 50-fold, or more. The period of time to induce quiescence in proliferating cells may be, for example, at least about 6 hours, at least about 12 hours, at least 18 hours, at least about 24 hours, at least about 36 hours, at least about 48 hours.

In some embodiments cultures and/or transplantation of quiescent stem cells is performed in the presence of artificial muscle fiber (AMF) as a substrate. A population of AMF may have an average diameter of from about 10 to about 100 μm, e.g. from about 25 to about 75 μm, and may be around about 50 mm in diameter. A population of AMF may have an average length of from about 50 mm to about 5000 mm, e.g. from about 100 mm to about 1000 mm and may be around about 500 μm. Diameter and length can be varied according to culture conditions. In some embodiments the AMF is a hydrogel. In some embodiments the AMF is a collagen-based hydrogel. The elasticity of the AFM may be adapted to the stem cell of interest. In one embodiment the elasticity of an AFM for muscle stem cells is from about 0.8 to about 2.5 kPA, and may be from about 1 to about 2 kPA. The AFM substrate can be present with respect with medium in ratios varying from 10:0 to 6:4. An AFM substrate is optionally modified by, e.g. functionalization with adhesion molecules, including without limitation integrin, coating with laminin, and the like.

Embodiments of the invention include a composition of quiescent cells in quiescence medium, optionally in combination with AFM substrate. The cells may be induced quiescent cells. In some embodiments, a composition of quiescent cells is provided, where the cells have been maintained in culture for at least about 12 hours, at least about 24 hours, at least about 36 hours, at least about 48 hours. In some such embodiments the cell have been genetically modified in culture. In some embodiments the purified cell population is provided in a pharmaceutically acceptable excipient for transplantation, and may be provided in an effective dose for transplantation, e.g. at least about $10^5$ cells, at least about $10^6$ cells, at least about $10^7$ cells, at least about $10^8$ cells or more.

In some embodiments of the invention, methods are provided for maintaining stem cells in a quiescent state, the method comprising obtaining quiescent stem cells, e.g. from an in vivo source; and culturing the cells in quiescence medium of the invention, optionally in combination with AFM substrate. In other embodiments are provided for inducing a quiescent phenotype in proliferating stem or progenitor cells, e.g. in myoblasts, the method comprising obtaining proliferating stem or progenitor cells, e.g. from an in vivo source or from cells expanded in vitro; and culturing the cells in quiescence medium of the invention, optionally in combination with AFM substrate. In some such embodiments the method further comprising contacting the cells with a polynucleotide for genetic modification, where the cells are genetically modified. In some embodiments the methods further comprise transplanting the cells to an individual. In some embodiments the transplantation is autologous.

BRIEF DESCRIPTION OF THE DRAWINGS

FIG. 1B Analysis of single MuSC transcriptional profiles. Single freshly isolated MuSCs were isolated by FACS and compared for gene expression profiles using PCA. Single MuSCs were isolated from TA muscles at 0, 1.5, or 3.5 days post injury (DPI). Standard deviational ellipses (radius=1 SD) are shown for 0 and 3.5 DPI. FIG. 1C Analysis of combinatorial screening of quiescence-preserving molecules. The graph shows the correlation between transcriptional profiles generated for each group of 500 MuSCs grown in different combinations of the compounds tested. The combination that showed the highest correlation with QMuSCs (Y axis) and the lowest correlation with MuSCs cultured in GM (X axis) was the one chosen for the QM (indicated by the arrow). FIG. 1D Quantification of the areas, assessed microscopically, of MuSCs cultured in either GM or QM immediately after isolation (0 days) or after 2.5 days in culture (n=3). FIG. 1E Representative immunofluorescence images of FACS isolated MuSCs cultured for 2.5 days in GM or QM.

FIG. 2A-2H. Artificial muscle fibers support functional quiescence of MuSCs in vitro FIG. 2A Cultured MuSCs in different media quantified at different time points. MuSCs that were freshly isolated by FACS (left panel) or isolated associated with single myofiber explants (right panel) were cultured in QM for different days before switching the medium to GM to assess their responsiveness to activate and proliferate. Myogenic cells are cells that stained positive with a cocktail of Pax7 and MyoD antibodies (n=3). FIG. 2B Schematic of the fabrication process of AMFs on a microfluidic chip. The design is based on arrays of 20 chambers (500 µm×300 µm×7 mm), with media inlet and outlet ports for fluidic lines constituted by 5 parallel channels (50×50 µm) used to exchange solutions and to perform cell seeding through the chambers. Monomers of Collagen I are extruded through a nozzle in the chambers to generate AMFs. FIG. 2C Representative immunostaining of a single myofiber (top) and a single AMF (bottom). Scanning electron microscopy images (insets) show MuSCs localized on the fibers. Scale bar=50 µm. FIG. 2D Representative confocal immunofluorescence images of a functionalized AMF cross-section. Immunostaining was performed for Collagen I, Integrin $\alpha 4\beta 1$ and Laminin. Scale bar=50 µm. FIG. 2E Quantification of MuSCs cultured onto AMFs in different media at different time points. Freshly isolated MuSCs were associated with AMFs and cultured in QM or GM as in FIG. 2A. FIG. 2F Quantification of MuSCs that were $EdU_{+ve}$ after switching QM to GM at day 3.5. Freshly isolated MuSCs, associated with a native fiber, associated with an AMF, or not associated with a fiber, were cultured in QM in the presence of EdU and switched to GM before being stained. FIG. 2G ATP level quantification measured in a bioluminescence assay. Cultured cells were analyzed and compared to freshly isolated quiescent MuSCs. Freshly isolated MuSCs, with or without being associated with AMFs, were cultured in QM or GM for 2.5 days before being analyzed (10,000 cells per condition). FIG. 2H PCA of single cell transcriptional profiles. Single MuSCs cultured, with or without being associated with AMFs, in different media were compared with freshly isolated quiescent or activated MuSCs. Clouds represent the densitometry of single cell distributions; colors indicate different cell populations.

FIG. 3A-3F. MuSCs cultured in QM on AMFs are transcriptionally similar to quiescent MuSCs in vivo FIG. 3A Multidimensional scaling representation for the training dataset of single MuSC gene expression. The analysis is based on the proximity matrix of the proportion of trees in which cell pairs share terminal nodes. FIG. 3B Generation of a random forest model for single MuSCs. After combinatorial Q-RT-PCR on single cells, random forest construction was performed using the gene expression profiles of 48 cells 0 DPI and 68 cells 3.5 DPI. FIG. 3C Cross-validation dataset. Data are analyzed from a separate experiment, which also included 1.5 DPI cells, to validate the random forest performance in predicting and recognizing the MuSC quiescent or activated state. FIG. 3D Classification of cells in three conditions (isolated and grown in GM; isolated and grown in QM; associated with AMFs and grown in QM) as being in either a "quiescent" or an "activated" state based on the single cell gene expression profile of individual MuSCs. After this model construction and validation, single cells from one of three culture conditions (GM, QM, or AMF+ QM) were classified as 0 DPI ("Q") or 3.5 DPI ("A"). FIG. 3E Loadings for genes expressed in single MuSCs. The analysis was performed after combinatorial Q-RT-PCR on cells 0 DPI (for quiescent MuSCs) or on cells 1.5 or 3.5 DPI (for activated MuSCs). The most important genes whose expression is correlated with and predictive of the quiescent state are shown. FIG. 3F Violin plots for selected genes expressed in single $MuSC_{S64,65}$. The graphs compare the results from single MuSCs obtained in different conditions in vivo (QMuSCs; AMuSCs 1.5 DPI; AMuSCs 3.5 DPI) and in vitro (QM+AMF; QM−AMF). Dots represent the median. Black bars represent the first and third quartiles. Whiskers represent the minimum and maximum within 1.5 interquartile distances of the first or third quartile.

FIG. 4A-4E. Transplant potency enhancement via the artificial niche FIG. 4A Results of non-invasive in vivo bioluminescence imaging of freshly isolated, transplanted MuSCs. MuSCs (100 cells per condition) were isolated and immediately transplanted into preinjured TA muscles: 1) still associated with native myofibers; 2) isolated by FACS and plated onto AMFs in vitro prior to transplantation; or 3) isolated by FACS and in suspension (n≥4). FIG. 4B Results of non-invasive in vivo bioluminescence of pre-cultured, transplanted MuSCs. MuSCs were cultured for 2.5 days in QM, associated or not with a fiber as in FIG. 4A, prior to transplantation (50 cells per condition) and imaged weekly for one month (n=5). FIG. 4C Representative bioluminescence images of a time course analysis of one of the host mice, quantified as in FIG. 4B, that received 50 MuSCs transplanted in each TA muscles. The right leg (which is on the right side since the mouse is prone in each image) received MuSCs associated with AMFs; the left leg received MuSCs not associated with any fiber. Images were obtained at different time points as indicated (bioluminescence values are indicated as photons $cm_{-2\ s-1}$ on the scale to the right). FIG. 4D Representative immunofluorescence immunohistochemistry (IF-IHC) of Luciferase expression in TA muscle cross sections. Muscles of the mice imaged and quantified in FIG. 4B and FIG. 4C were isolated 40 days after transplantation. Scale bars=100 µm. FIG. 4E Quantification of IF-IHC staining for $Luciferase_{+ve}$ fibers per cluster in TA muscles that were recipients of transplanted MuSCs. The average number of fibers per cluster per TA is shown; the number of clusters/TA was: Native Fibers 4.6±1.02; AMF 2.6±1.02; No Fiber 0.4±0.48.

FIG. 5A-5D. AMF maintains MuSC self-renewal capacity after in vitro manipulations FIG. 5A IF-IHC staining of TA muscles transplanted with MuSCs associated with AMFs showing representative images of transplanted $Luciferase_{+ve}$ MuSCs ($Luciferase_{+ve}$ MuSCs localized in between $Luciferase_{+ve}$ fibers are indicated by arrows and magnified in the insets). Scale bars=100 µm. FIG. 5B Results of non-invasive in vivo bioluminescence imaging of muscles that were recipient of transplanted $Luciferase_{+ve}$ MuSCs and re-injured after 40 days (indicated by the arrow) after the transplantation. The second injury was performed to test if the bioluminescence signal increased as a consequence of activating and expanding $Luciferase_{+ve}$ MuSCs that were initially transplanted and that had engrafted under the basal lamina (n≥4). FIG. 5C Quantification of the number of transplanted MuSCs expressing YFP that engrafted as stem cells. Cells were isolated and cultured in QM prior to transplantation in TA muscles. An injury was induced 40 days after transplantation. Ten days later, the percentage of MuSCs ($VCAM_{+ve}$) that were donor derived ($YFP_{+ve}$) was assessed by FACS. FIG. 5D Results of non-invasive in vivo bioluminescence imaging of transduced and transplanted MuSCs. Isolated MuSCs were either cultured in QM while associated with AMFs or cultured in GM alone for 3.5 days. During culturing, cells were transduced with a lentivirus expressing Luciferase, and 1,000 cells were then transplanted into pre-injured TA muscles. Recipient mice were imaged by bioluminescence 30 days later.

FIG. 6B Scanning electron microscopy images show hMuSC localized on a human AMF. Scale bar=100 µm. The box is magnified (inset) to show the hMuSC. FIG. 6C Immunostaining of a single human AMF seeded with hMuSCs. Scale bar=10 µm. FIG. 6D Reversible quiescence of hMuSCs cultured on AMFs in QM. Freshly isolated hMuSCs were associated with AMFs and cultured in QM before switching to GM (as in FIG. 2a). FIG. 6E Quantification of hMuSCs that were $EdU_{+ve}$ after switching QM to GM at 2.5 days. Freshly isolated hMuSCs, associated with AMFs, were cultured in QM and switched to GM, pulsing EdU for 24 hours before being stained (n=3). FIG. 6F Results of non-invasive in vivo bioluminescence imaging of transduced and transplanted hMuSCs. Similar to experiments of FIG. 5d, isolated hMuSCs were transduced to express Luciferase then either cultured in QM while associated with AMFs or cultured in GM alone for 3.5 days and then transplanted into TA muscles.

FIG. 7B Topological data analysis (TDA) of single MuSCs freshly isolated by FACS. TDA was used to identify the quiescent signature—in an unsupervised fashion (see Methods) within single cell populations. Nodes in the network correspond to collections of samples, and edges connect two nodes where samples exist in both nodes; edge distance does not carry any meaning in this representation. Node size is correlated with the number of samples in each node, and the coloring corresponds to Pax7 expression levels, with a gradient signifying low-to-high.

FIG. 10B Representative immunofluorescence images of FACS isolated MuSCs cultured for 72 hours on microposts of 2 kPa or 12 kPa. FIG. 10C Percentages of quiescent (i.e. EdU-ve) MuSCs cultured on microposts of different elasticity. Freshly FACS isolated MuSCs were cultured for 72 hours. A pulse of EdU was administered to the cells for the last 12 hours. Twenty-two fields per condition in three technical replicates were counted (error bars are s.e.m.). FIG. 10D Representative immunofluorescence images of FACS isolated MuSCs cultured for 72 hours on microposts. Two differently labeled MuSCs (one is $Pax7_{+ve}/MyoD_{-ve}$ and the other is $Pax7_{-ve}/MyoD_{+ve}$) are shown. FIG. 10E Percentages of $Pax7_{+ve}$ or $MyoD_{+ve}$ cells cultured for 72 hours on microposts of different elasticity as shown in "d". In this experiment, 50 fields per condition in three technical replicates were counted (error bars are s.e.m.).

FIG. 11B Percentages of $EdU_{+ve}$ MuSCs cultured on Collagen-based hydrogels generated using different formulations, as in FIG. 11A. MuSCs were freshly isolated by FACS and cultured for 36 hours in the presence of EdU (error bars are s.e.m., n=3). FIG. 11C Percentages of $Caspase_{+ve}$ MuSCs on Collagen based hydrogels generated using different formulations, as in FIG. 11A. MuSCs were freshly isolated by FACS and cultured for 36 hours (error bars are s.e.m., n=3).

FIG. 12B Percentages of proliferating MuSCs cultured alone or on AMFs. Cells were cultured in the presence of EdU for 48 hours (error bars are s.e.m., n=3). FIG. 12C Micro-tensile mechanical stress capacity measurements of AMFs. (Left panel) Representative micrographs of the experimental set up, showing the cantilever (above) used to clip and pull an AMF (visible in the middle and indicated by the arrow in the lower right panel) and the manipulator used to hold the AMF below the cantilever. (Right panel) Measurements of AMF tensile mechanical stress capacity expressed in Pa are shown (Young's Modulus is Et=26.9 kPa).

FIG. 13A-13D. Integrin α4β1 is a component of the niche that promotes quiescence of MuSCs FIG. 13A Representative images of IF-IHC staining of an uninjured TA muscle showing in cross section myofibers that are Integrin $α4β1_{+ve}$. FIG. 13B Representative images of immunofluorescence staining of single myofiber explants showing Integrin $α4β1_{+ve}$ staining in proximity to a MuSC. Individual myofibers were dissociated and immediately fixed. Percentages of $EdU_{+ve}$ FIG. 13C or $Caspase_{+ve}$ FIG. 13D MuSCs plated on different Integrins at different concentrations. FACS-isolated MuSCs were cultured for 36 hours on substrates coated with different concentrations of Integrin heterodimers (error bars are s.e.m., n=3).

FIG. 14B ATP measurements of FACS-isolated MuSCs cultured on differently functionalized AMFs for 36 hours (10,000 cells were analyzed per condition in three biological replicates, error bars are s.e.m.). FIG. 14C Myogenic progression of FACS-isolated MuSCs cultured on AMFs with different functionalization. MuSCs were stained for Pax7 and MyoD to assess their state in the myogenic progression from quiescence after 72 hours in culture (error bars are s.e.m., n=3). FIG. 14D Percentages of $EdU_{+ve}$ MuSCs cultured on Collagen-based soft thick hydrogels or on rigid substrates with a thin Collagen coating, generated at different Collagen formulations and similarly functionalized with Integrin and Laminin proteins. MuSCs were freshly isolated by FACS and cultured for 36 hours in the presence of EdU (error bars are s.e.m., n=3).

FIG. 16. Quiescence media formulation Serum-free "quiescence medium" (QM) formulation that best maintained the transcriptional signature of quiescence for at least two days in culture among all conditions analyzed. Using a combinatorial Q-RT-PCR array strategy for a set of 93 genes (see methods), we found conditions in which cultured MuSCs were very similar to freshly isolated quiescent MuSCs.

DESCRIPTION OF THE SPECIFIC EMBODIMENTS

Figure 1A:
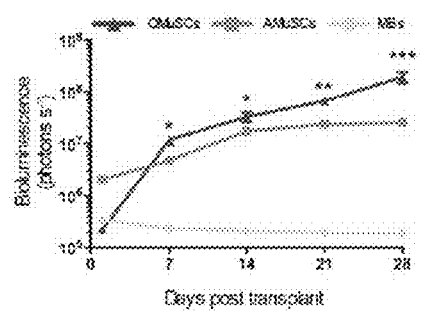
FIG. 1A-1E. Formulation and functional characterization of "quiescence medium" (QM) FIG. 1A Non-invasive bioluminescence of transplanted myogenic cells. Quiescent MuSCs (QMuSCs), activated MuSCs (AMuSCs) or cultured myoblasts (MBs) expressing luciferase were transplanted (10,000 cells per condition) in pre-injured TA muscles and host mice were imaged weekly using an IVIS in vivo bioluminescence imaging system for up to four weeks (n=6).

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims.

As used herein the singular forms "a", "an", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

Stem cell: The term stem cell is used herein to refer to a mammalian cell that has the ability both to self-renew, and to generate differentiated progeny (see Morrison et al. (1997) Cell 88:287-298). Generally, stem cells also have one or more of the following properties: an ability to undergo asynchronous, or asymmetric replication, that is where the two daughter cells after division can have different phenotypes; extensive self-renewal capacity; capacity for existence in a mitotically quiescent form; and clonal regeneration of all the tissue in which they exist, for example the ability of hematopoietic stem cells to reconstitute all hematopoietic lineages. "Progenitor cells" differ from stem cells in that they typically do not have the extensive self-renewal capacity, and often can only regenerate a subset of the lineages in the tissue from which they derive Stem cells may be characterized by both the presence of markers associated with specific epitopes identified by antibodies and the absence of certain markers as identified by the lack of binding of specific antibodies. Stem cells may also be identified by functional assays both in vitro and in vivo, particularly assays relating to the ability of stem cells to give rise to multiple differentiated progeny.

Somatic Stem cells: Somatic stem cells reside in differentiated tissue, but retain the properties of self-renewal and the ability to give rise to multiple cell types, usually cell types typical of the tissue in which the stem cells are found. Numerous examples of somatic stem cells are known to those of skill in the art, including, but not limited to, muscle stem cells (including without limitation satellite cells as described above), hematopoietic stem cells, neural stem cells, mesenchymal stem cells, pancreatic stem cells, hepatic stem cells, cardiac stem cells, kidney stem cells, liver stem cells.

Stem cells of interest include muscle stem cells, which may be evidenced by the ability to engraft and repopulate the myofiber-associated compartment in vivo following intramuscular injection, and subsequent maintenance of myogenic-colony forming capacity. Muscle cells include skeletal, cardiac and smooth muscles, but particularly skeletal muscle.

The term "proliferative status" as used herein refers to whether a population of cells or a subpopulation thereof, are dividing and thereby increasing in number, in the quiescent state, or whether the cells are not proliferating, dying or undergoing apoptosis. For example, the population of cells may be hematopoietic stem or progenitor cells, or a subpopulation thereof.

The terms "modulating the proliferative status" or "modulating the proliferation" as used herein refers to the ability of a compound to alter the proliferation rate of a population of cells. A compound may be toxic, wherein the proliferation of the cells is slowed or halted, or the proliferation may be enhanced such as, for example, by the addition to the cells of a cytokine or growth factor.

The term "quiescent" as used herein refers to cells that are not actively proliferating by means of the mitotic cell cycle. Quiescent cells (which include cells in which quiescence has been induced as well as those cells which are naturally quiescent, such as certain fully differentiated cells) are generally regarded as not being in any of the four phases G1, S, G2 and M of the cell cycle; they are usually described as being in a G0 state, so as to indicate that they would not normally progress through the cycle. Cultured cells can be induced to enter the quiescent state by the methods of the invention, or by methods including, but not limited to, chemical treatments, nutrient deprivation, growth inhibition or manipulation of gene expression, and induced to exit the quiescent state by contacting the cells with a compound, such as a cytokine or growth factor.

The term "muscle cell" as used herein refers to any cell which contributes to muscle tissue. Myoblasts, satellite cells, myotubes, and myofibril tissues are all included in the term "muscle cells". Muscle cell effects may be induced within skeletal, cardiac and smooth muscles. Muscle tissue in adult vertebrates will regenerate from reserve myoblasts called "satellite cells", or mesangioblasts, bone marrow derived cells, muscle interstitial cells, mesenchymal stem cells, etc. Satellite cells are distributed throughout muscle tissue and are mitotically quiescent in the absence of injury or disease. Following muscle injury or during recovery from disease, satellite cells will reenter the cell cycle, proliferate and 1) enter existing muscle fibers or 2) undergo differentiation into multinucleate myotubes, which form new muscle fiber. The myoblasts ultimately yield replacement muscle fibers or fuse into existing muscle fibers, thereby increasing fiber girth by the synthesis of contractile apparatus components. This process is illustrated, for example, by the nearly complete regeneration which occurs in mammals following induced muscle fiber degeneration; the muscle progenitor cells proliferate and fuse together regenerating muscle fibers.

One example of muscle stem cells is cells characterized as $CD45^-$, $CD11b^-$, $CD31^-$, $Sca1^-$, $\alpha7$ integrin$^+$, and $CD34^+$. In some embodiments, muscle stem cells cultured on the elastic substrate described herein may be implanted into a recipient subject mammal, wherein the cells or population of cells differentiate into muscle cells, e.g. for regeneration.

Regeneration as used herein may refer to the process by which new cells form from progenitor cells. Progenitor cells include, but are not limited to, stem cells, multipotent cells, pluripotent cells, primary cells or cell lines, reprogrammed cells, transdifferentiated cells, dedifferentiated or induced pluripotent stem cells, including without limitation myoblasts. Such cells may be manipulated ex vivo and transplanted to a recipient for regeneration, where the cells can be delivered in a suitable medium; contained in a substrate of the invention, etc.

Muscle regeneration as used herein refers to the process by which new muscle fibers form from muscle progenitor cells. A therapeutic composition will usually confer an increase in the number of new fibers by at least 1%, more preferably by at least 20%, and most preferably by at least 50%. The growth of muscle may occur by the increase in the fiber size and/or by increasing the number of fibers. The growth of muscle may be measured by an increase in wet weight, an increase in protein content, an increase in the number of muscle fibers, an increase in muscle fiber diameter; etc. An increase in growth of a muscle fiber can be defined as an increase in the diameter where the diameter is defined as the minor axis of ellipsis of the cross section.

Muscle regeneration may also be monitored by the mitotic index of muscle. For example, cells may be exposed to a labeling agent for a time equivalent to two doubling times. The mitotic index is the fraction of cells in the culture which have labeled nuclei when grown in the presence of a tracer which only incorporates during S phase (i.e., BrdU) and the doubling time is defined as the average S time required for the number of cells in the culture to increase by a factor of two. Alternatively, activation in vivo may be detected by monitoring the appearance of the intermediate filament vimentin by immunological or RNA analysis methods. When vimentin is assayed, a useful activator may cause expression of detectable levels of vimentin in the muscle tissue when the therapeutically useful dosage is provided. Productive muscle regeneration may be also monitored by an increase in muscle strength and agility.

Muscle regeneration may also be measured by quantitation of myogenesis, i.e. fusion of myoblasts to yield myotubes. An effect on myogenesis results in an increase in the fusion of myoblasts and the enablement of the muscle differentiation program. For example, the myogenesis may be measured by the fraction of nuclei present in multinucleated cells in relative to the total number of nuclei present. Myogenesis may also be determined by assaying the number of nuclei per area in myotubes or by measurement of the levels of muscle specific protein by Western analysis.

The survival of muscle fibers may refer to the prevention of loss of muscle fibers as evidenced by necrosis or apoptosis or the prevention of other mechanisms of muscle fiber loss. Muscles can be lost from injury, atrophy, and the like, where atrophy of muscle refers to a significant loss in muscle fiber girth.

The terms "grafting", "engrafting", and "transplanting" and "graft" and "transplantation" as used herein refer to the process by which stem cells or other cells according to the present disclosure are delivered to the site where the cells are intended to exhibit an effect, such as, but not limited to, repairing damage to a patient's central nervous system, treating autoimmune diseases, treating diabetes, treating neurodegenerative diseases, or treating the effects of nerve, muscle and/or other damage caused by birth defects, stroke, cardiovascular disease, a heart attack or physical injury or trauma or genetic damage or environmental insult to the body, caused by, for example, disease, an accident or other activity. The stem cells or other cells for use in the methods of the present disclosure can also be delivered in a remote area of the body by any mode of administration as described herein. For example, the term "cell engraftment" as used herein can refer to the process by which cells such as, but not limited to, muscle stem cells, are delivered to, and become incorporated into, a differentiated tissue such as a muscle, and become a part of that tissue. For example, muscle stem cells, when delivered to a muscle tissue, may proliferate as stem cells, and/or may bind to skeletal muscle tissue, differentiate into functional myoblasts cells, and subsequently develop into functioning myofibers. Transplantation may utilize a dose of cells effective to obtain the desired effect, which may be delivered in an appropriate medium or substrate, including an elastic substrate of the invention.

Stem cell environment. The tissue in which stem cells are normally resident may be referred to as a native microenvironment, or niche. Typically the in vivo environment will include physical properties, e.g. elasticity, fluid flow, fibrous proteins that contact the cells, etc.; and may further include biochemical factors that interact with stem cells to regulate stem cell fate. In many cases, the localization (locale) of the niche within the tissue is known, although not always. In most cases, the precise components of stem cell niches remain unknown. Within adult tissue, stem cell niches maintain adult stem cells in a typically quiescent state, but after tissue injury, the surrounding micro-environment actively produces signals to promote self-renewal or differentiation to form new tissues, the process of regeneration. Niche variables include, but are not limited to, cell-cell interactions between stem cells; interactions between stem cells and neighboring differentiated cells; interactions between stem cells and adhesion molecules; extracellular matrix components; oxygen tension; growth factors; cytokines, and physiochemical nature of the environment including the pH, etc. The physical parameters of the niche with respect to substrate elasticity may be determined empirically, or may be determined from published references (for example see Engler et al. (2006) Cell 126:677).

Within a niche, stem cells are frequently anchored to a basal lamina or stromal cells that can provide a substrate for oriented cell division. The basal lamina is a regulator of the accessibility of growth factors and other signals, as associated extracellular matrix (ECM) molecules and glycoproteins can both concentrate and sequester factors in inactive or active forms. Cell anchoring may orient cell division resulting in the segregation of key determinants into one or both daughter cells depending on the plane of division.

Muscle stem cell niche. Muscle stem cells are typically sandwiched between the basement membrane and sarcolemma (cell membrane) of individual muscle fibers, and can be difficult to distinguish from the sub-sarcolemmal nuclei of the fibers. These cells are able to differentiate and fuse to augment existing muscle fibers and to form new fibers. (see Boonen and Post (2008) Tissue Eng Part B Rev. 14(4):419-31; Cosgrove et al. (2010) Differentiation Review; and Lutolf, Gilbert, Blau (2010) Nature Review.

Tissue Elasticity. In the methods of the invention, the elasticity of the substrate is selected to have physiological parameters, for example properties similar to the elasticity of the tissue from which the cell is derived or normally resident. Elasticity may be measured by any convenient method, as is known in the art. For example see, inter alia, Kaletunc et al. (1991) Food Hydrocolloids 5:237-247; Krall and Weitz (1998) Physical Review Letters 80:778-781; Melekaslan et al. (2003) Polymer Bulletin 50:287-294; each herein incorporated by reference. For example, a shear rheometer may be used to measure the elasticity of the substrate. In some cases the elastic moduli of these environments have not been measured, however it will be apparent to those familiar with measurements of biomechanical properties of tissues that it is currently possible to measure the elastic modulus of these structures, for example using rheological instruments or atomic force microscopy.

The term "mimics" or "approximates" the elasticity of the natural environment refers to an elastic substrate that provides for an elasticity that is general equivalent in range to the native environment of the cell or tissue in question, as discussed herein. The substrate of the invention may be within a range that is not more than 3 standard deviations from the range of the native environment, not more than 2 standard deviations from the range of the native environment, not more than 1 standard deviations from the range of the native environment. Alternatively the range may be not more than 2× different from the high or low value of the native environment; not more than 3× different from the high or low value of the native environment; not more than 5× different from the high or low value of the native environment; not more than 10× different from the high or low value of the native environment.

In some embodiments, the elasticity of the substrate will vary, depending on the specific somatic stem cell that is being cultured. For example, it is found the muscle stem cells are optimally grown on a substrate of at least about 1 kPa and not more than about 50 kPa, usually at least about 5 kPa and not more than about 25 kPa, and may be from about 7.5 to about 15 kPa. Similar elasticity may be utilized for stem cells residing in other soft tissue niches, e.g. neural stem cells, hematopoietic stem cells, liver stem cells, etc. Hard tissues, such as bone, may have a more rigid structure, e.g. at least about 100 kPa and up to as much as $10^6$ kPa. Aged and diseased tissues will typically have moduli of elasticity which are 0-80% higher than young or healthy tissue.

The elasticity range for a reproductive cell may be 0.01-80 kPa. The following elasticity ranges are appropriate for elastic substrates used to culture cells derived from, adapted to, or intended for the indicated tissue types: zona pellucida (0.5-50 kPa (Murayama, 2006; Khalilian, 2010; Sun, 2003)); endometrium (0.01-10 kPa); fallopian tube (0.01-10 kPa); uterus (5-40 kPa); vagina (3-15 kPa (Epstein, 2007)); testes (1-80 kPa); ovaries (0.1-80 kPa).

The elasticity range for a primary cell or cell line may be 0.001-250 kPa. The following elasticity ranges are appropriate for elastic substrates used to culture cells derived from, adapted to, or intended for the indicated tissue types: bone marrow (0.001-2 kPa; Winer, 2009); lens (10-150 kPa (Ziebarth, 2011)); brain (0.01-0.5 kPa (Ommaya, 1968)); cornea (130-250 kPa (Tanter, 2009)); bladder (0.1-10 kPa); spleen (0.1-10 kPa); small intestine (0.1-10 kPa); colon (0.01-10 kPa); rectum (0.01-10 kPa); lung (0.1-10 kPa); hair follicles (5-25 kPa (Pailler-Mattei et al. 2008)); pancreas (0.1-30 kPa); smooth muscle (2-100 kPa).

Elasticities of interest also include skeletal muscle (2-24 kPa (relaxed); 90-120 kPa (tensed)(Kwiatkowska et al. 2009)); kidney (1-5 kPa (Levental et al. 2007)); cardiac muscle (25-120 kPa (Mathur et al. 2001)); endothelium (1-7 kPa (Mathur et al. 2001)); liver (0.3-9 kPa); adipose tissue (5-100 Pa (Levental et al. 2007)) thyroid (5-15 kPa (Levental et al. 2007)); articular cartilage (0.5-1.5 MPa (Levental et al. 2007)); blood (<0.1 kPa (fluid)); skin (5-25 (Pailler-Mattei et al. 2008)); mammary fatty tissue (10-35 kPa (Krouskop et al. 1998)); mammary glandular tissue (14-49 kPa (Krouskop et al. 1998)); mammary gland (50-500 Pa (Levental et al. 2007)) prostate (30-70 kPa, (Krouskop et al. 1998)); lymph node (50-500 Pa).

The term "polymeric composition" as used herein refers to a single compound species or a mixture of compound species that may be cross-linked to form a polymer. Such precursor compounds include, but are not limited to, such as poly(ethylene glycol), polyaliphatic polyurethanes, polyether polyurethanes, polyester polyurethanes, polyethylene copolymers, polyamides, polyvinyl alcohols, polypropylene glycol, polytetramethylene oxide, polyvinyl pyrrolidone, polyacrylamide, poly(hydroxyethyl acrylate), and poly(hydroxyethyl methacrylate), collagen, hyaluronic acid, chitosan, dextran, agarose, alginate, protein polymers, methylcellulose and the like. The polymer compounds before polymerization may be toxic to, or otherwise inhibit the proliferation of a vertebrate cell, but it will be understood by those in the art that when polymerized, the polymer will be inert with respect to any cell or cell line in contact with the polymer.

In some embodiments of the invention, the hydrogel composition may comprise a polymer (or combination of polymers) selected from the group consisting of: a poly(ethylene glycol), a polyaliphatic polyurethane, a polyether polyurethane, a polyester polyurethane, a polyethylene copolymer, a polyamide, a polyvinyl alcohol, a polypropylene glycol, a polytetramethylene oxide, a polyvinyl pyrrolidone, a polyacrylamide, a poly(hydroxyethyl acrylate), a poly(hydroxyethyl methacrylate), poly (glycolic acid), poly (DL-lactic-co-glycolic acid), polyhydroxyalkanoate, poly(4-hydroxybutirate), sulfonated polymers, polygluconic acid, poly(acrylic acid), polyphosphazenes, polysaccharides, proteins, collagen, elastin, alginate, fibrin, fibronectin, laminin, hyaluronic acid, or another biologically-occurring polymer, polypeptide sequences cleavable by proteases including matrix metalloproteases, or copolymers formed from monomers of one or more of these.

The elasticity of the substrate may be influenced by a variety of factors, including, but not limited to, the branching of the polymer, the concentration of polymer, and the degree of cross-linking. For example, where the polymer is formed of polyethylene glycol vinyl sulfone (PEG-VS), the length of the PEG monomer and the branching, e.g. 2 arm, 4 arm, 8-arm, and the like may be varied to achieve the desired elasticity. In some embodiments, a non-swelling hydrogel is used.

Hydrogels of the invention optionally comprise at least one structural protein associated with a stem cell niche, e.g. fibronectin, laminin, collagen, and the like. Alternatively, or in combination, other proteins that have a beneficial or desired effect on the stem cells may be included in the hydrogel. Proteins may be conjugated to the hydrogel through a linker. The term "tether" or "linker" may refer to a molecular structure that conjugates a protein or polypeptide to the hydrogel. It is contemplated that a linker molecule suitable to link a biomolecule to the hydrogels of the disclosure can be, but is not limited to, a maleimide' PEG-SVA linker; a dicarboxylic acid that further includes at least one available group, such as an amine group, for conjugating to a prosthetic group; and the like. It is also contemplated that other functional side groups may substitute for the amine group to allow for the linking to selected peptides. Exemplary dicarboxylic acids include, but are not limited to, aspartate, glutamate, and the like, and can have the general formula $(HOOC)-(CH_2)_n-(CHNH_2^+)-(CH_2)_m-(COOH)$, where n and m are each independently 0, or an integer from 1 to about 10. It is further considered within the scope of the disclosure for the linker to be a multimer, or a combination, of at least two such dicarboxylic acids. For example, such linker molecules may include, but are not limited to, $(aspartate)_x$, $(glutamate)_y$, or a combination thereof, where adjacent amino acids can be joined by peptide bonds, and the like. The subscripts x and y are each independently 0, or an integer from 1 to about 12.

Culture medium: The cells are grown in vitro in an appropriate liquid nutrient medium. Generally, the seeding level will be at least about 10 cells/ml, more usually at least about 100 cells/ml and generally not more than about $10^5$ cells/ml, usually not more than about $10^4$ cells/ml. Cells may be cultured singly or in groups.

Various media are commercially available and may be modified for the invention. Specific examples are provided in FIG. 16. Commercial media include Ex vivo serum free medium, Dulbecco's Modified Eagle Medium (DMEM), MCDB, RPMI, Iscove's medium, etc. Appropriate antibiotics to prevent bacterial growth and other additives, including, but not limited to, pyruvate (0.1-5 mM), glutamine (0.5-5 mM), 2-mercaptoethanol ($1-10\times10^{-5}$ M) may also be included. The medium may be any conventional culture medium, generally supplemented with one or more of Elcatonin at a concentration of from about 0.1 to 10 μM, SB203580 at a concentration of from about 1 to about 100 μM, SU5402 at a concentration of from about 0.1 to 10 μM, Forskolin at a concentration of from about 0.1 to 10 μM, TGFbeta at a concentration of from about 0.5 to 25 nM, Knock Out SR at a concentration of from about 0.1 to about 10%, and may be around 2% to about 5%, and Insulin-transferrin-selenium (ITS, Invitrogen) at a concentration of from about 0.1 to about 10%, and may be around 2% to about 5%. Exemplary media are provided FIG. 16.

The term "cell culture" or "culture" means the maintenance of cells in an artificial, in vitro environment. Culture conditions may include, without limitation, a specifically dimensioned container, e.g. flask, roller bottle, plate, 96 well plate, etc.; culture medium comprising suitable factors and nutrients for growth of the desired cell type; and a substrate on the surface of the container or on particles suspended in the culture medium. By "container" is meant a glass, plastic, or metal vessel that can provide an aseptic environment for culturing cells.

The terms "primary culture" and "primary cells" refer to cells derived from intact or dissociated tissues or organ fragments. A culture is considered primary until it is passaged (or subcultured) after which it is termed a "cell line" or a "cell strain." The term "cell line" does not imply homogeneity or the degree to which a culture has been characterized. A cell line is termed "clonal cell line" or "clone" if it is derived from a single cell in a population of cultured cells. Primary cells can be obtained directly from a human or animal adult or fetal tissue, including blood. The primary cells may comprise a primary cell line, or such as, but not limited to, a population of muscle satellite cells.

Substrate. This disclosure provides artificial muscle fibers for use in the culture and transplantation of quiescent stem cells, particularly quiescent muscle stem cells. Artificial muscle fibers may be a collagen hydrogel. As used herein, a substrate refers to a semi-solid matrix capable of being contacted by cells in a culture condition.

Preferred substrates for the methods of the invention are hydrogels. The term "hydrogel" as used herein refers to a network of polymer chains that are water-insoluble, sometimes found as a colloidal gel in which water is the dispersion medium. Hydrogels can contain over 99% water and may comprise natural or synthetic polymers, or a combination thereof. In other instances, hydrogels may contain other percentages of water, as described herein. Hydrogels also possess a degree of flexibility due to their significant water content. A detailed description of suitable hydrogels may be found in published US patent application 20100055733, herein specifically incorporated by reference in its entirety for all purposes. The cell culture platform of the present disclosure may be fabricated from a soft and inert substrate that imbibes large amounts of water, thus approximating critical physicochemical aspects of the stem cell niche.

In some instances, the cell culture substrate is a hydrogel, a cell-free scaffold, a foam rubber, a soft plastic, a gel, a putty, an aerogel, a fabric, a paste, an oil, or a wax. In some cases, the cell culture substrate is primarily made up of water. The cell culture substrate may further comprise one or more channels through the substrate or wells on top of the substrate. For example, a cell may be placed on top of a channel or inside of a well on the cell culture substrate. The channels through the cell culture substrate may also allow perfusion of solutions through the cell culture substrate. The channels may allow the perfusion of an oxygenated cell culture media through the cell culture substrate. In some cases, a mold may be placed in contact with the precursor solution while it is curing, and then removed from the cell culture substrate. For example, the cell culture substrate or substrates may be fabricated outside of the container and then placed in the container.

A cell culture substrate may be a hydrogel comprising a polymer selected from a group comprising polyethylene glycol, poly(vinyl acetate), poly(ethylene acrylate), polyaliphatic polyurethane, polyether polyurethane, polyester polyurethane, polyethylene copolymer, polyamide, polyvinyl alcohol, polypropylene glycol, polytetramethylene oxide, polyvinyl pyrrolidone, polyacrylamide, poly(hydroxyethyl acrylate), poly(hydroxyethyl methacrylate), poly (glycolic acid), poly (DL-lactic-co-glycolic acid), polyhydroxyalkanoate, poly(4-hydroxybutirate), sulfonated polymers, polygluconic acid, poly(acrylic acid), polyphosphazenes, polysaccharides, proteins, collagen, elastin, alginate, fibrin, fibronectin, laminin, hyaluronic acid, or another biologically-occurring polymer, polypeptide sequences cleavable by proteases including matrix metalloproteases, or copolymers formed from monomers of one or more of these. For example, the hydrogel substrate may be comprised of polyamide monomers. In another example, the hydrogel substrate may comprise a combination of polyvinyl pyrrolidone and polyacrylamide. The hydrogel may also be polymerized from highly polydisperse precursors. For example, the hydrogel may be polymerized from polyethylene glycol vinyl sulfone precursors of varying sizes. The hydrogel may be a non-swelling hydrogel. But in some cases, the hydrogel is a swelling hydrogel.

In some instances, the polymer may comprise a chemically modified monomer, said monomer being substituted with, but not limited to, a sulfhydryl, vinyl sulfone, carboxylic acid, alcohol, vinyl, ester, thiol, or bromine group. For example, the polymer may comprise a hyaluronic acid substituted with a thiol group. In another example, the polymer may comprise a polyethylene glycol substituted with an ester group. In another example, the hydrogel polymer is composed of at least two different polyethylene glycol monomers. For example, the hydrogel may comprise polyethylene glycol sulfhydryl (PEG-SH) monomer and polyethylene glycol vinyl sulfone (PEG-VS) monomer.

The hydrogel substrate may be produced by reacting one or more polymers. For example, the hydrogel substrate is produced by reacting polyacrylamide monomers. In another example, the hydrogel substrate is produced by reacting hyaluronic acid and poly(vinyl acetate). In another example, the elastic hydrogel substrate is produced by reacting at least two polyethylene glycol compounds. For example, the sulfhydryl groups on 4-armed PEG (PEG-SH) are reacted with the vinyl sulfone groups on 8-armed PEG (PEG-VS) to produce the hydrogel substrate.

The water composition in the hydrogel substrate may vary. Hydrogels can contain over 70% water. Hydrogels can contain over 71% water. Hydrogels can contain over 72% water. Hydrogels can contain over 73% water. Hydrogels can contain over 74% water. Hydrogels can contain over 75% water. Hydrogels can contain over 76% water. Hydrogels can contain over 77% water. Hydrogels can contain over 78% water. Hydrogels can contain over 79% water. Hydrogels can contain over 80% water. Hydrogels can contain over 81% water. Hydrogels can contain over 82% water. Hydrogels can contain over 83% water. Hydrogels can contain over 84% water. Hydrogels can contain over 85% water. Hydrogels can contain over 90% water. Hydrogels can contain over 95% water. Hydrogels can contain over 99% water.

The hydrogel substrate is sufficiently thick to mask the physical properties of a container, device or tool. The hydrogel substrate is at least 5 µm thick. The hydrogel substrate is at least 10 µm thick. The hydrogel substrate is at least 20 µm thick. The hydrogel substrate is at least 30 µm thick. The hydrogel substrate is at least 40 µm thick. The hydrogel substrate is at least 50 µm thick. The hydrogel substrate is at least 100 µm thick. The hydrogel substrate is at least 200 µm thick. The hydrogel substrate is at least 300 µm thick. The hydrogel substrate is at least 400 µm thick. The hydrogel substrate is at least 500 µm thick. The hydrogel substrate is at least 1000 µm thick. The hydrogel substrate is at least 2000 µm thick. The hydrogel substrate is at least 3000 µm thick. The hydrogel substrate is at least 4000 µm thick. The hydrogel substrate is at least 5000 µm thick.

In some instances, the elasticity of the cell culture substrate (e.g., hydrogel) may be tuned (e.g., the elasticity of the substrate may be increased or decreased). In some cases, the tunability can be performed by the use of bonds which are unstable and therefore break over time. For example, the elasticity of the substrate can be tuned by the use of covalent bonds, ionic bonds, van der Waal's bonds, or any combination thereof. In other instances, the tunability can be performed by the use of chemical moieties which form bonds over time. For example, the addition of a polypeptide may decrease the elasticity of the substrate (e.g., make it more rigid). The elasticity of the substrate may be tuned by the addition or removal of ions or molecules which stabilize or destabilize bonds in the substrate. For example, the addition or removal of a biomolecule, such as collagen to, may cause a change in elasticity. The elasticity of the substrate may also be varied by the addition, removal, activation, or inactivation of enzymes which digest or form bonds in the substrate. Heating or cooling the elastic substrate is also another method to alter the elasticity of the substrate. For example, heating the substrate may increase the elasticity of the substrate (e.g. increase its flexibility). The elasticity of the substrate may also be modified by exposure to light which lyses or aids formation of bonds in the substrate. Exposure of the substrate to a catalyst which accelerates the formation of breakage of bonds in the substrate may also alter the elasticity of the substrate. Changes in ionic strength or pH of the cell culture medium may also be used to tune the elasticity of the substrate. The elasticity of the substrate may also be tuned by altering the composition. For example, a cell culture substrate comprising a hydrogel may be tuned by changing the polymer concentration (e.g., 0.01% polymer, 2% polymer, 5% polymer, etc). The elasticity of the substrate may also be tuned by modifying the length of the monomer. For example, varying the length of the polyethylene glycol monomer may increase or decrease the elasticity of the cell culture substrate. The cell culture substrate may also be tuned by modifying the branching of the polymer. For example, using a 2-arm, 4-arm, or 8-arm polyethylene glycol vinyl sulfone.

The elasticity of the cell culture substrate may be tuned before, during, or after the addition of a cell, biomolecule, or chemical. For example, the cell culture substrate may be tuned by the breakage of hydrogen bonds before the addition of a biomolecule. In another example, the cell culture substrate may be tuned by heating after the addition of the chemical. In another example, the cell culture substrate by be tuned by changing the pH of the cell culture media throughout the cell culturing process.

The elasticity of the hydrogel substrate may be tuned to sufficiently culture the cell on the hydrogel substrate. The elasticity of the hydrogel substrate may range from 0.01 kPa to 2000 kPa. For example, the elasticity range for culturing an endometrium cell may be 0.01 kPa to 10 kPa. In another example, elasticity range for culturing a smooth muscle cell may be 2 kPa to 100 kPa. In another example, the elasticity range for culturing an articular cartilage cell may be 500 kPa to 1500 kPa.

The elasticity of the hydrogel substrate may be varied before, during, or after the seeding of the cells. In some cases, the elasticity is varied over time while the cells are in culture. For example, the elasticity may be varied over the course of 1 minute, over the course of 10 minutes, over the course of 1 hour, over the course of 1 week, over the course of 1 month, over the course of 2 months, over the course of 3 months, over the course of 4 months, over the course of 5 months, over the course of 6 months, etc. The elasticity may be increased by 5% or more, by 10% or more, by 15% or more, or by 20% or more, in some instances by 30% or more, by 40% or more, or by 50%, in some instances by more than 50%, e.g. by 60% or more, by 70% or more, by 80% or more, by 90% or more, by 100% or more, sometimes by more than 100%, e.g. by 200% or more. The elasticity may be decreased by 5% or more, by 10% or more, by 15% or more, or by 20% or more, in some instances by 30% or more, by 40% or more, or by 50%, in some instances by more than 50%, e.g. by 60% or more, by 70% or more, by 80% or more, by 90% or more, by 100% or more, sometimes by more than 100%, e.g. by 200% or more.

Elastic substrates (e.g., hydrogels) may also be patterned with regions of different elasticities. For example, the cell culture substrate may have an elasticity of 0.1 kPa in one region and an elasticity of 4 kPa in another region. and may be formed in a variety of shapes, e.g. cilia, folds, crypts, striations, processes, dimples, partial spherical shells, and bumps, which optionally mimic a native environment of the cell. The substrate may also be subjected to twisting, compressing, stretching, or otherwise deforming the elastic substrate during culture. Medium may be added to the substrate prior to, or at the time when cells are brought into contact. Cells may be deposited on a substrate surface, sandwiched between two or more substrates with similar or different elasticities, or encapsulated in the substrate for both in vitro and in vivo purposes.

The hydrogel substrate may further comprise a biomolecule, chemical, or any combination thereof linked to its surface. The biomolecule may be, but is not limited to, a protein, a polypeptide, a peptide, a nucleic acid molecule, a nucleotide, an oligonucleotide, a polynucleotide, a saccharide, a polysaccharide, a cytokine, a growth factor, a morphogens, an antibody, a peptibody, or any fragment thereof. The cytokine may be without limitation erythropoietin, granulocyte-macrophage colony stimulating factor, granulocyte colony stimulating factor, macrophage colony stimulating factor, thrombopoietin, stem cell factor, interleukin-1, interleukin-2, interleukin-3, interleukin-6, interleukin-7, interleukin-15, Flt3L, leukemia inhibitory factor, insulin-like growth factor, insulin, or any fragment thereof. The morphogens may be, but are not limited to, transforming growth factor beta (TGF-beta), Hedgehog/Sonic Hedgehog, Wingless/Wnt, epidermal growth factor (EGF), and fibroblast growth factor (FGF), or any fragment thereof. Growth factors include, but are not limited to, fibroblast growth factor, epidermal growth factor, insulin-like growth factor 1, platelet-derived growth factor, nerve growth factor, transforming growth factor beta, or any fragment thereof. In some embodiments, the protein is selected from the native cellular environment or niche, including, but not limited, fibronectin, laminin, collagen, vitronectin, entactin, bone morphogenetic protein, bone morphogenetic protein ligand, E-cadherin, extracellular matrix proteins, or any fragment thereof.

Methods

The present disclosure provides methods and compositions for culturing cells. In some cases, the cell is a primary cell, stem cell, transdifferentiated cell, dedifferentiated cell, reprogrammed cell, multipotent cell, or pluripotent cell. In some cases, the cell is a stem cell; in other cases, the cell is not a stem cell. The cell can be any cell of the body, including, but not limited to: muscle cell, hematopoietic cell, lymphocyte, mononuclear cell, neural cell, mesenchymal cell, pancreatic cell, hepatic cell, heart cell, kidney cell, liver cell, skeletal muscle cell, mammary cell, mammary gland cell, endothelial cell, adipose tissue cell, thyroid cell, articular cartilage, skin cell, prostate cell, blood cell, retinal cell, dental pulp, bladder cell, spleen cell, small intestine cell, colon, rectal cell, lung, hair follicles, intestinal cell, or bone marrow.

The cells are preferably human but can also be non-human, e.g., non-human mammals. Examples of non-human mammals include, but are not limited to, non-human primates (e.g., apes, monkeys, gorillas), rodents (e.g., mice, rats), cows, pigs, sheep, horses, dogs, cats, or rabbits. Similarly, the cell can be from any organism, reptile, microbe, or microorganism. Often, the cells are derived from a human subject or human patient. The subject may be free of a disease or disorder, or the subject may suffer from a disease or disorder, or at risk for such disease or disorder. Examples of diseases are provided herein. The subject may be a female; in some cases, the subject is a male. In some cases, the subject is a female over, or under, the age of 20, 25, 30, 35, 40, 41, 42, 43, 44, 45, 50, or 55. In some cases, the subject is a male over, or under, the age of 20, 25, 30, 35, 40, 41, 42, 43, 44, 45, 50, or 55.

As described herein, in certain embodiments, the cell is a stem cell. A stem cell includes, but is not limited to, an embryonic stem cell, a somatic stem cell, an induced pluripotent stem cell, a multipotent stem cell, or certain germ cells (e.g., gametocyte). In some cases, the somatic stem cell is a muscle cell, hematopoietic cell, lymphocyte, mononuclear cell, neural cell, mesenchymal cell, pancreatic cell, hepatic cell, heart cell, kidney cell, liver cell, skeletal muscle cell, mammary cell, mammary gland cell, endothelial cell, adipose tissue cell, thyroid cell, articular cartilage, skin cell, prostate cell, blood cell, retinal cell, dental pulp, bladder cell, spleen cell, small intestine cell, colon, rectal cell, lung, hair follicles, intestinal cell, or bone marrow.

Treatment regimens may utilize a short-term administration of the active agent; although the treatment may be repeated as necessary. The treatment regime can require administration for prolonged periods, but may be administered as a single dose monthly, semi-monthly, etc. The size of the dose administered must be determined by a physician and will depend on a number of factors, such as the nature and gravity of the disease, the age and state of health of the patient and the patient's tolerance to the drug itself.

Diseases of interest for treatment with the methods of the invention include heritable and acquired muscle disorders, e.g. of skeletal muscle. A number of muscle conditions in which there is muscle wasting such as cachexia, atrophy and sarcopenia, are of interest, e.g. conditions associated with increased age, immobility, drug treatment, cancer, and the like. In addition to skeletal muscle formation, the regeneration of cardiac muscle in the aging is of interest. For example, following an event such as myocardial infarction; surgery, catheter insertion, atherosclerosis, and the like, cardiac muscle can be damaged. Such damage is not easily repaired in elderly patients, resulting in a loss of function.

The subject methods are useful for both prophylactic and therapeutic purposes. Thus, as used herein, the term "treating" is used to refer to both prevention of disease, and treatment of a pre-existing condition. The treatment of ongoing disease, to stabilize or improve the clinical symptoms of the patient, is a particularly important benefit provided by the present invention. Such treatment is desirably performed prior to loss of function in the affected tissues; consequently, the prophylactic therapeutic benefits provided by the invention are also important. Evidence of therapeutic effect may be any diminution in the severity of disease. The therapeutic effect can be measured in terms of clinical outcome or can be determined by immunological or biochemical tests.

In some embodiments, the inherited muscle disorders include, without limitation, muscular dystrophies. For example, Duchenne dystrophy is an X-linked recessive disorder characterized by progressive proximal muscle weakness with destruction and regeneration of muscle fibers and replacement by connective tissue. Duchenne dystrophy is caused by a mutation at the Xp21 locus, which results in the absence of dystrophin, a protein found inside the muscle cell membrane. It affects 1 in 3000 live male births. Symptoms typically start in boys aged 3 to 7 yr. Progression is steady, and limb flexion contractures and scoliosis develop. Firm pseudohypertrophy (fatty and fibrous replacement of certain enlarged muscle groups, notably the calves) develops. Becker muscular dystrophy is a less severe variant, also due to a mutation at the Xp21 locus. Dystrophin is reduced in quantity or in molecular weight. Patients usually remain ambulatory, and most survive into their 30s and 40s.

In some embodiments, muscle disorders include myopathies. In some embodiments, myopathies include, but are not limited to, congenital and metabolic myopathies, including glycogen storage diseases and mitochondrial myopathies. Congenital myopathies are a heterogeneous group of disorders that cause hypotonia in infancy or weakness and delayed motor milestones later in childhood. An autosomal dominant form of nemaline myopathy is linked to chromosome 1 (tropomyosin gene), and a recessive form to chromosome 2. Other forms are caused by mutations in the gene for the ryanodine receptor (the calcium release channel of the sarcoplasmic reticulum) on chromosome 19q. Skeletal abnormalities and dysmorphic features are common. Diagnosis is made by histochemical and electron microscopic examination of a muscle sample to identify specific morphologic changes.

Mitochondrial myopathies range from mild, slowly progressive weakness of the extraocular muscles to severe, fatal infantile myopathies and multisystem encephalomyopathies. Some syndromes have been defined, with some overlap between them. Established syndromes affecting muscle include progressive external ophthalmoplegia, the Kearns-Sayre syndrome (with ophthalmoplegia, pigmentary retinopathy, cardiac conduction defects, cerebellar ataxia, and sensorineural deafness), the MELAS syndrome (mitochondrial encephalomyopathy, lactic acidosis, and stroke-like episodes), the MERFF syndrome (myoclonic epilepsy and ragged red fibers), limb-girdle distribution weakness, and infantile myopathy (benign or severe and fatal). Muscle biopsy specimens stained with modified Gomori's trichrome stain show ragged red fibers due to excessive accumulation of mitochondria. Biochemical defects in substrate transport and utilization, the Krebs cycle, oxidative phosphorylation, or the respiratory chain are detectable. Numerous mitochondrial DNA point mutations and deletions have been described, transmitted in a maternal, nonmendelian inheritance pattern. Mutations in nuclear-encoded mitochondrial enzymes occur.

Glycogen storage diseases of muscle are a group of rare autosomal recessive diseases characterized by abnormal accumulation of glycogen in skeletal muscle due to a specific biochemical defect in carbohydrate metabolism. These diseases can be mild or severe. In a severe form, acid maltase deficiency (Pompe's disease), in which 1,4-glucosidase is absent, is evident in the first year of life and is fatal by age 2. Glycogen accumulates in the heart, liver, muscles, and nerves. In a less severe form, this deficiency may produce proximal limb weakness and diaphragm involvement causing hypoventilation in adults. Myotonic discharges in paraspinal muscles are commonly seen on electromyogram, but myotonia does not occur clinically. Other enzyme deficiencies cause painful cramps after exercise, followed by myoglobinuria. The diagnosis is supported by an ischemic exercise test without an appropriate rise in serum lactate and is confirmed by demonstrating a specific enzyme abnormality.

Channelopathies are neuromuscular disorders with functional abnormalities due to disturbance of the membrane conduction system, resulting from mutations affecting ion channels. Myotonic disorders are characterized by abnormally slow relaxation after voluntary muscle contraction due to a muscle membrane abnormality.

Myotonic dystrophy (Steinert's disease) is an autosomal dominant multisystem disorder characterized by dystrophic muscle weakness and myotonia. The molecular defect is an expanded trinucleotide (CTG) repeat in the 3' untranslated region of the myotonin-protein kinase gene on chromosome 19q. Symptoms can occur at any age, and the range of clinical severity is broad. Myotonia is prominent in the hand muscles, and ptosis is common even in mild cases. In severe cases, marked peripheral muscular weakness occurs, often with cataracts, premature balding, hatchet facies, cardiac arrhythmias, testicular atrophy, and endocrine abnormalities. Mental retardation is common. Severely affected persons die by their early 50s.

Myotonia congenita (Thomsen's disease) is a rare autosomal dominant myotonia that usually begins in infancy. In several families, the disorder has been linked to a region on chromosome 7 containing a skeletal muscle chloride channel gene. Painless muscle stiffness is most troublesome in the hands, legs, and eyelids and improves with exercise. Weakness is usually minimal. Muscles may become hypertrophied. Diagnosis is usually established by the characteristic physical appearance, by inability to release the handgrip rapidly, and by sustained muscle contraction after direct muscle percussion.

Familial periodic paralysis is a group of rare autosomal dominant disorders characterized by episodes of flaccid paralysis with loss of deep tendon reflexes and failure of muscle to respond to electrical stimulation. The hypokalemic form is due to genetic mutation in the dihydropyridine receptor-associated calcium channel gene on chromosome 1q. The hyperkalemic form is due to mutations in the gene on chromosome 17q that encodes a subunit of the skeletal muscle sodium channel (SCN4A).

Sarcopenia is a term utilized to define the loss of muscle mass and strength that occurs with aging. Sarcopenia is believed to play a major role in the pathogenesis of frailty and functional impairment that occurs with old age. Progressive muscle wasting occurs with aging. The prevalence of clinically significant sarcopenia is estimated to range from 8.8% in young old women to 17.5% in old men. Persons who are obese and sarcopenic (the "fat frail") have worse outcomes than those who are sarcopenic and non-obese. There is a disproportionate atrophy of type IIa muscle fibers with aging. There is also evidence of an age-related decrease in the synthesis rate of myosin heavy chain proteins. Motor units innervating muscle decline with aging, and there is increased irregularity of muscle unit firing. There are indications that cytokines, especially interleukin-1beta, tumor necrosis factor-alpha, and interleukin-6, play a role in the pathogenesis of sarcopenia. Similarly, the decline in anabolic hormones, i.e. testosterone, dehydroepiandrosterone growth hormone, and insulin-like growth factor-1, is also implicated in the sarcopenic process.

Sarcopenia is typically marked by a decrease in the circumference of distinct types of muscle fibers. During sarcopenia, there is a decrease in "type 2" fiber circumference (Type 11), with little to no decrease in "type I" fiber circumference (Type 1). Diagnosis of sarcopenia may include low muscle mass, >2 standard deviations below that mean measured in young adults (aged 18-39 years in the 3rd NHANES population) of the same sex and ethnic background, and low gait speed (e.g. a walking speed below 0.8 m/s in the 4-m walking test).

Cachexia is wasting of both adipose and skeletal muscle. It occurs in many conditions and is common with many cancers when remission or control fails. Some cancers, especially pancreatic and gastric cancers, cause profound cachexia. Affected patients may lose 10 to 20% of body weight. Men tend to experience worse cachexia with cancer than do women. Neither tumor size nor the extent of metastatic disease predicts the degree of cachexia. Cachexia is associated with reduced response to chemotherapy, poor functional performance, and increased mortality.

The primary cause of cachexia is not anorexia or decreased caloric intake. Rather, this complex metabolic condition involves increased tissue catabolism. Protein synthesis is decreased and degradation increased. Cachexia is mediated by certain cytokines, especially tumor necrosis factor-$\alpha$, IL-1b, and IL-6, which are produced by tumor cells and host cells in the tissue mass. The ATP-ubiquitin-protease pathway plays a role as well.

Corticosteroid induced myopathy. Steroid muscle-related involvement is a frequent but often underestimated adverse effect of steroid treatment. Clinical presentation may differentiate two features: the less frequent, represented by acute myopathy, essentially observed in resuscitation, in patients treated with high dosages, and the more frequent feature, insidious, painless, chronic myopathy, characterized by a progressive proximal deficit. Diagnosis is mostly based on the clinic, muscle biopsy should remain exceptional, performed to detect other myopathies, since there are no specific anatomopathological findings. Muscle enzymes are rarely increased, electrophysiological analyses demonstrate unspecific and variable abnormalities. Pathophysiology of steroid-induced myopathy is multifactorial, related to protein metabolism modifications (change of both metabolism and catabolism), cellular transcription, growth factors (IGF-1, myostatine).

Unlike with other drug-induced myopathies, serum CK concentration does not markedly increase with steroid myopathy. EMG is normal or may show low amplitude myopathic motor unit potentials and no signs of neuropathy. Muscle biopsy usually reveals an increased variation in the diameter of fibers and type IIb muscle fiber atrophy without muscle fiber inflammation or necrosis. However, a necrotizing steroid myopathy has also been reported to occur. Proximal muscle weakness of the lower and upper extremities is significantly related to the cumulative dose of steroid. An increase in muscle strength occurring 3-4 weeks after dose reduction usually indicates steroid-induced myopathy. However, chronic myopathy may persist after prolonged treatment with high doses of corticosteroids.

Genetic Alteration of Quiescent Cells

Cells induced or maintained under quiescent conditions according to the methods of the invention can be genetically engineered, e.g. to correct molecular defects. In some embodiments, autologous cells are genetically corrected and reintroduced into the individual to provide for correction of genetic defects. The cells may be expanded in culture before induction of quiescence.

In cell-based gene therapy, affected human cells are isolated, cultured, and genetically modified ex vivo through non-viral or viral vector-mediated gene transfer. The modified cells are usually enriched and then reinfused into patients to realize therapeutic effects. In this way, human body is not directly exposed to gene delivery vectors, which may improve safety and target cell specificity. In addition, the cells that undergo desired modification can be selected and maintained as quiescent cells by the methods of the invention to enhance efficacy. Autologous cells isolated from a patient but genetically modified cab be used to treat him/herself.

Vectors for this purpose include, for example, DNA (non-viral) vectors and viral vectors. Circular plasmid DNA can enter cells in its naked form, or being covered with chemicals to enhance stability and delivery efficiency. Viral vectors take advantage of the infectious nature and gene-shuttling capability of certain viruses Both types of vectors can directly deliver genes into human body.

DNA (non-viral) vectors. A therapeutic gene expression cassette is typically composed of a promoter that drives gene transcription, the transgene of interest, and a termination signal to end gene transcription. Such an expression cassette can be embedded in a plasmid (circularized, double-stranded DNA molecule) as delivery vehicle. Plasmid DNA (pDNA) can be directly injected by a variety of injection techniques, including hydrodynamic injection. To help negatively charged pDNA molecules penetrate the hydrophobic cell membranes, chemicals including cationic lipids and cationic polymers have been used to condense pDNA into lipoplexes and polyplexes, respectively. These nanoparticles shield pDNA from nuclease degradation in extracellular space and facilitate entry into target cells.

Viral vectors. Many mammalian viruses have been explored as gene delivery vectors. Replacing most of the viral genes with a therapeutic gene cassette, and meanwhile retaining signal sequences that are essential for in vitro replication and packaging in producer cell lines formulate the common theme of viral vector genome engineering. Viral vector production commonly employs a trans-packaging system in cell culture, requiring the co-existence of one to four components. Vectors based on gammaretrovirus, lentivirus, adenovirus (AdV), adeno-associated virus (AAV) and herpes simplex virus (HSV) are among the most widely used viral vectors.

Gammaretrovirus and lentivirus are both retrovirus, which is characterized by an RNA genome, and utilizing virus-derived reverse transcriptase and integrase to insert their proviral complementary DNA into the host genome. Gammaretrovirus can only transduce replicating cells, whereas lentivirus can also transduce non-replicating cells, which makes lentiviral vector more favorable in many gene therapy settings. Vector development based on these two viruses has greatly benefited from engineering their envelope glycoproteins that are amenable to modification for specific tissue and/or cell tropisms.

For targeted gene delivery to a specific cell type, retroviral vectors can be pseudotyped with a viral glycoprotein that binds to a specific membrane receptor of that cell type. Furthermore, a viral glycoprotein can be fused with a ligand protein or antibody that recognizes cell type-specific surface molecules, providing a versatile way of cell type-specific gene delivery. Integration into host genome, the distinctive feature of retroviral vectors, ensures the stability of transgene and persistent transgene expression in daughter cells following genome replication and cell division. Most retroviral vectors are based on a self-inactivating (SIN) vector design. In SIN vector design, the enhancer/promoter sequences in LTR are removed, thus greatly reducing the likelihood of activating oncogenes. Other approaches aiming at reducing the risk of insertional mutagenesis include the development of integration-deficient lentiviral vectors by mutating the integrase, and site-directed integration using zinc finger nuclease.

In contrast to retrovirus, AdV contains a DNA genome that episomally resides in host nucleus, which prevents insertional mutagenesis. AdV is able to transduce a broad range of quiescent and proliferating human cells. Currently, the most commonly used AdV vectors are derived from AdV serotype 5 (AdV5).

AAV is a group of small, simple, helper-dependent, non-pathogenic, and single-stranded DNA viruses. Recombinant AAV (rAAV) vector carrying inverted terminal repeats as the only viral component entered the gene therapy arena much later than retroviral and AdV vectors, but have quickly gained popularity. For rAAV vectors, it is largely the capsid that determines the tropism and transduction profile in different cell types. Tropism of several natural AAV capsids has been well characterized in mouse and larger animal models. In addition to relying on natural diversity, AAV capsids can be decorated by peptides or "shuffled" to generate novel capsids that suit specific needs. Similar to AdV vector, rAAV vector can transduce both dividing and non-dividing cells, and its recombinant viral genome stays in host nucleus predominantly as episome.

Expression of transposase mediates a cut-and-paste mechanism that efficiently inserts a designer transposon harboring a transgene cassette into host genome. The DNA transposon/transposase system can be delivered in vivo or ex vivo in the simple form of plasmid DNA. Instead of inserting extra DNA material into host genome, another approach to permanently correcting a diseased genome is through targeted genomic editing. Designer DNA endonucleases such as the CRISPR/Cas system can be engineered to cut genomic DNA in a sequence-specific manner, allowing for disruption or repair of that region. The genes orchestrating this process need only to be transiently expressed in cultured cells, whereas the mark in the genome is left permanent.

Additional nucleic acid delivery protocols of interest include, but are not limited to: those described in U.S. Patents of interest include 5,985,847 and 5,922,687 (the disclosures of which are herein incorporated by reference); WO/11092; Acsadi et al., New Biol. (1991) 3:71-81; Hickman et al., Hum. Gen. Ther. (1994) 5:1477-1483; and Wolff et al., Science (1990) 247: 1465-1468; etc.

The term "unit dosage form," as used herein, refers to physically discrete units suitable as unitary dosages for human and animal subjects, each unit containing a predetermined quantity of cells and substrates for transplantation of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

The cultured cells expanded by the methods of the invention can be supplied in the form of a pharmaceutical composition, comprising an isotonic excipient prepared under sufficiently sterile conditions for human administration. Choice of the cellular excipient and any accompanying elements of the composition will be adapted in accordance with the route and device used for administration. The composition may also comprise or be accompanied with one or more other ingredients that facilitate the engraftment or functional mobilization of the cells. Suitable ingredients include matrix proteins that support or promote adhesion of the cells.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

EXPERIMENTAL

Example 1

A Bioengineered Niche Preserves Stem Cell Quiescence and Enhances Therapeutic Potential Promising therapeutic approaches for genetic disorders involves isolating patients' stem cells, correcting genetic defects ex vivo, and reintroducing the cells in vivo to restore tissue function. A major challenge is the loss of stem cell potency during ex vivo manipulation. We sought to maintain muscle stem cells (MuSCs) in vitro in a potent, quiescent state. Using a machine learning method, we identified a molecular signature that was used in combinatorial screening of factors that could maintain MuSC quiescence, thus defining a "quiescence medium" (QM). We also designed artificial muscle fibers (AMFs), engineered to mimic the native MuSC niche. MuSCs associated with AMFs and maintained in QM in vitro could be genetically modified with lentiviral vectors and showed enhanced engraftment and self-renewal upon transplantation. Finally, we employed human MuSCs and were able to replicate the results obtained with murine cells. Transplantable biomimetic microenvironments may provide new therapeutic options in regenerative medicine.

To overcome this problem, we developed a system that combines two strategies: a defined culture condition that supports the maintenance of MuSC quiescence and a microscaffold that mimics the native niche. This combined method is capable of preserving MuSC quiescence without loss of proliferative and self-renewing capacities. We first developed an algorithm based on a machine learning strategy to identify a molecular signature of quiescence using the transcriptional profile of single cells. We used this signature in a screening to find a chemically defined quiescence medium (QM). We then engineered an artificial muscle fiber (AMF) based on a 3D microscaffold assembled from extracellular matrix (ECM) proteins found in the MuSC niche. We propose an approach in which we mimic the mechanical and biochemical properties of the native niche. Such an artificial niche was able to promote sustained quiescence of MuSCs. We then manipulated MuSCs in this system by transducing them with a lentivirus expressing luciferase and GFP. Following transplantation, MuSCs showed enhanced engraftment and self-renewal. Finally, we expanded the translational potential of our strategy by employing human MuSCs, to replicate the maintenance of quiescence in vitro and the enhanced engraftment in vivo. In this work, we demonstrate for the first time that the engineering of a culture system can be used to mimic the conditions of the "quiescent niche" in vivo, realizing the goal of creating the ex vivo conditions that maintain stem cell quiescence for a time sufficient to allow for genetic modification without compromising transplantation potency and efficacy. These findings demonstrate a utility for human stem cell therapy. These advances generate new tools to study the biology of MuSC quiescence and for improved stem cell therapeutics for muscle disorders ranging from traumatic injuries to genetic degenerative diseases such as the muscular dystrophies.

Maintenance of quiescence of MuSCs in vitro by soluble factors. It has been shown that cultured myogenic cells derived from MuSCs lose their potency after transplantation. While studying the quiescence of MuSCs, we observed that MuSCs, after isolation, exhibit a rapid loss of potency even after a short period of time in vitro. Using the Pax7Cre$_{ER}$ and the ROSA26$_{LuSEAP}$ mouse strains to genetically label MuSCs with the Luciferase reporter, we transplanted 10,000 MuSCs as "quiescent" MuSCs (immediately after isolation), "activated" MuSCs (cultured in vitro for 3.5 days), or "myoblasts" (cultured in vitro for 2 weeks). By imaging non-invasively the transplanted cells in vivo for 30 days, we found that quiescent MuSCs yielded the highest bioluminescence signal (FIG. 1a).

Figure 1B:
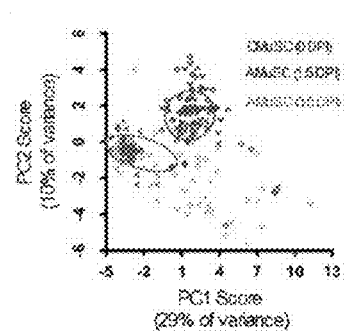
Figure 7A:
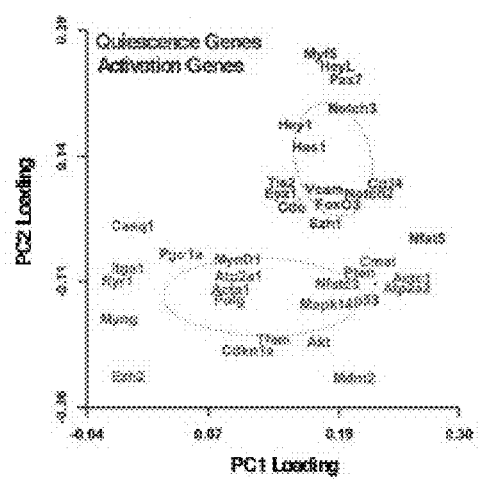
FIG. 7A-7B. Combinatorial Q-RT-PCR reveals genes predictive of quiescence and activation FIG. 7A Analysis of differential gene regulation between quiescent and activated single MuSCs. PCA loadings were generated for genes after combinatorial Q-RT-PCR of single MuSCs FACS isolated at 0, 1.5, and 3.5 DPI. Shown are standard deviational ellipses (radius=1 SD) after k-medians clustering with k=2.
Figure 7B:
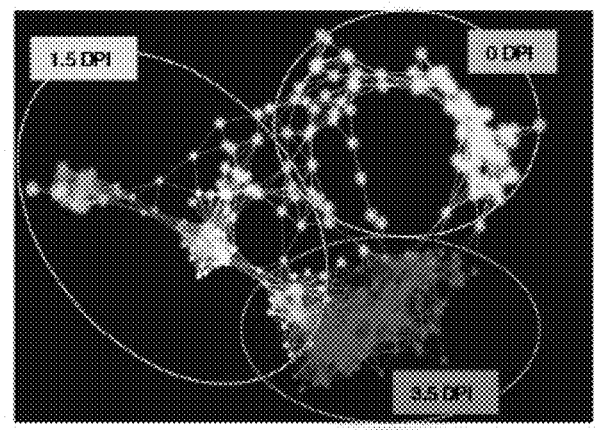

Based on these and previous data suggesting that quiescent cells may have the greater potency in this kind of transplantation assay over actively proliferating cells 1,2, we sought to define and engineer cell culture conditions that would maintain the quiescent state of freshly isolated MuSCs. We reasoned that such conditions would involve both the components of the medium as well as the nature of the substrate upon which cells were allowed to adhere. As such, we initially sought to develop a defined medium that would maintain MuSC quiescence in vitro. Toward this end, we sought to characterize a molecular signature of quiescent MuSCs that we could use to screen various media for their ability to maintain freshly isolated MuSCs in the quiescent state. We selected thirty-nine genes based on their relevance in the myogenic program and we performed a combinatorial Q-RT-PCR array analysis in a microfluidic chip to analyze single, freshly isolated quiescent MuSCs or single activated MuSCs that had been induced to proliferate for either 1.5 or 3.5 days in vivo by the injection of Cardiotoxin into the muscle, see for example Quarta, M. et al. An artificial niche preserves the quiescence of muscle stem cells and enhances their therapeutic efficacy. Nat. Biotechnol. 34, 752-759 (2016), herein specifically incorporated by reference. Principal component analysis (PCA) revealed that quiescent and activated MuSCs formed distinct transcriptional clusters (FIG. 1b). A separate analysis of the genes enriched in the two populations revealed clustering of genes highly expressed in quiescent MuSCs, defined here as "quiescence genes" (e.g., Pax7, Notch2, Notch3, Hes1, HeyL, Cd34, and Foxo3) and genes highly expressed in activated MuSCs, defined here as "activation genes" (e.g., Polg, p53, Ezh2, Myod) (FIG. 7a). At the single cell level, topological data analysis (TDA) identified a molecular signature characteristic of the quiescent MuSCs distinct from activated MuSC populations (FIG. 7b).

Figure 8:
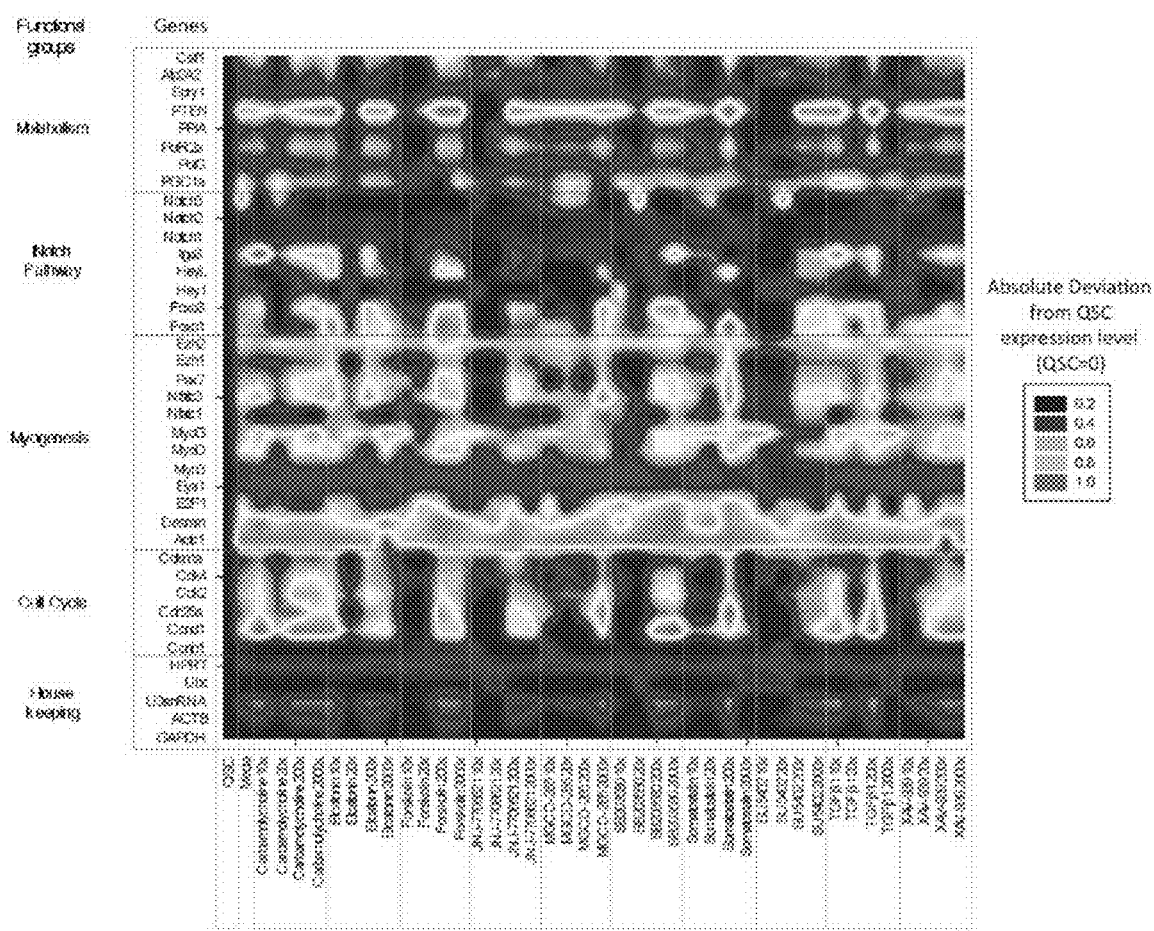
FIG. 8. Screening of molecules titrated at different concentrations. Heat map analysis of gene expression profiles obtained from MuSCs cultured in different concentrations of candidate molecules. In 96 well plates, 500 MuSCs were directly isolated by FACS and cultured in the presence of the candidate molecules titrated at different concentrations. After 2.5 days, cells were collected for combinatorial Q-RT-PCR to screen for the conditions that result mostly closely resemble freshly isolated MuSCs based on the gene expression profiles. A heat map for absolute deviations from expression levels of freshly isolated quiescent MuSCs (QSC) is shown. On the X axis, the molecules tested and the different dilutions employed from the working concentrations are indicated as in FIG. 16. On the Y axis the names of the genes that were tested are listed. The gene names were organized in general functional groups. Each functional group is based on the main function and role in MuSCs.

Knowing that quiescent MuSCs have a unique transcriptional signature, we employed combinatorial QRT-PCR to screen for molecules that, when added to the medium, would promote MuSC quiescence. From an initial panel of 50 compounds known or suggested in the literature to positively regulate cell quiescence, we selected the 10 molecules that showed the strongest propensity to prevent quiescent MuSC proliferation. We cultured 500 quiescent MuSCs for 2.5 days in the presence of different concentrations of these molecules, isolated RNA from the cells, and performed Q-RTPCR to assess the gene expression signatures of these cells (FIG. 8). Based on the results of this screening, we chose to further test Elcatonin, a Calcitonin Receptor ligand; Forskolin, an activator of cAMPo; SB203580, an inhibitor of p38; SU5402, an inhibitor of FGF receptor; and TGFβ. We also found a novel quiescence-promoting activity for Somatostatin, the c-Met inhibitor MGCD-265 and the CDK/Aurora inhibitor JMJ-7706621.

Figure 1C:
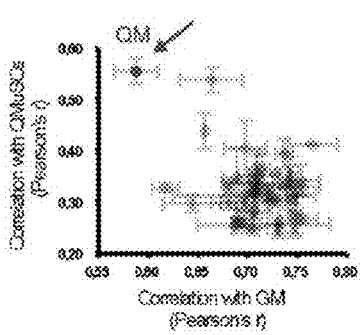
Figure 9:
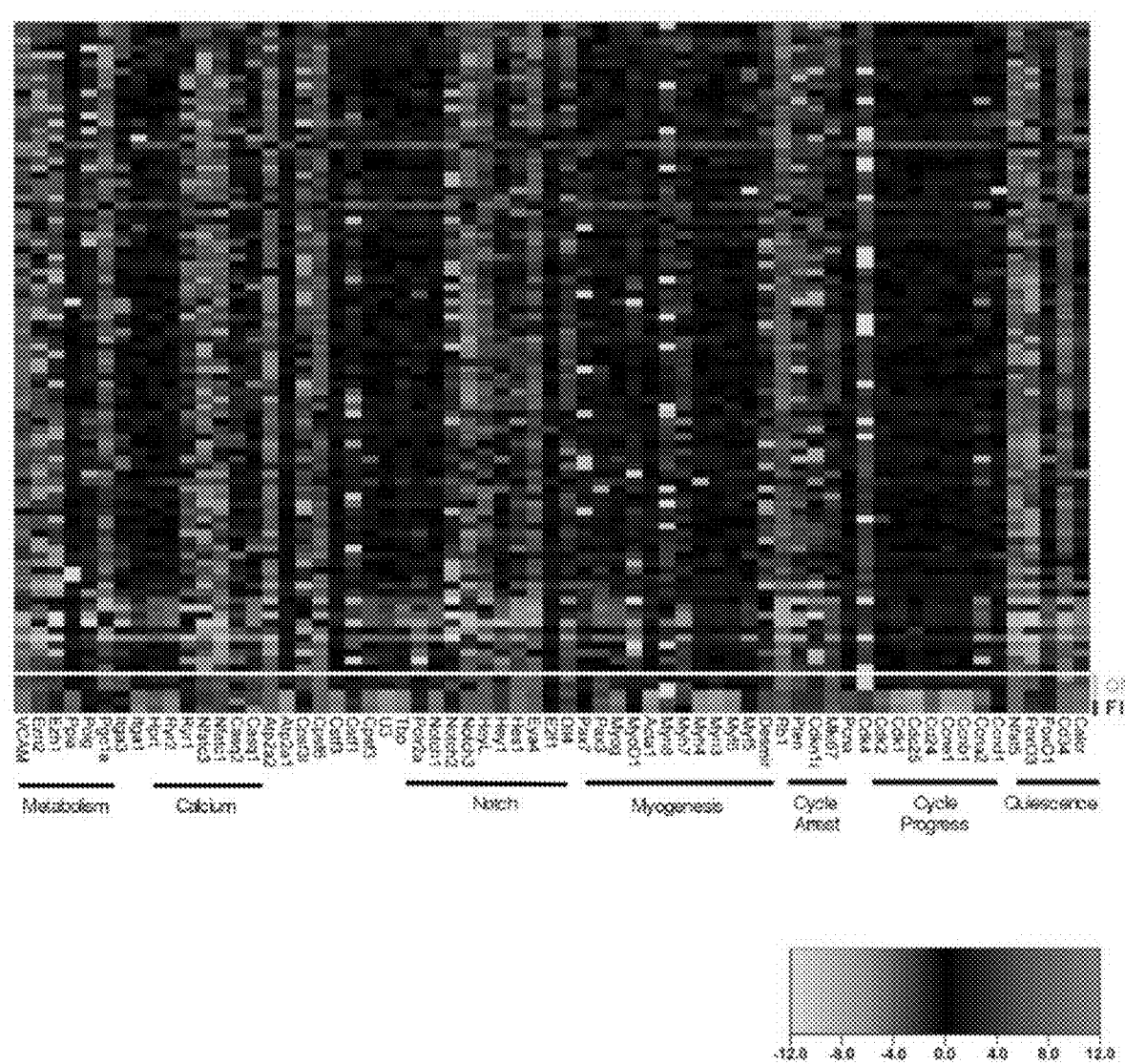
FIG. 9. Combinatorial screening of molecules a. Heat map analysis of gene expression profiles obtained from MuSCs cultured in different combinations of candidate molecules. Based on the panel of candidate molecules previously screened as in FIG. 8, a combinatorial screening for the top 8 molecules was performed on 500 FACS freshly isolated MuSCs cultured for 60 hours. Results are represented in a heat map clustering, based on Manhattan distance after UV-scaling and mean-centering genes Ward linkage. A line at the bottom of the heat map separates the profile of freshly isolated MuSCs (indicated on the right as FI) and MuSCs cultured in the combination of the 8 molecules that resulted in the gene expression prolife that was closest to that of freshly isolated MuSCs (indicated as QM). The scale bar (lower right) indicates the relative gene expression (Log 2).
Figure 10A:
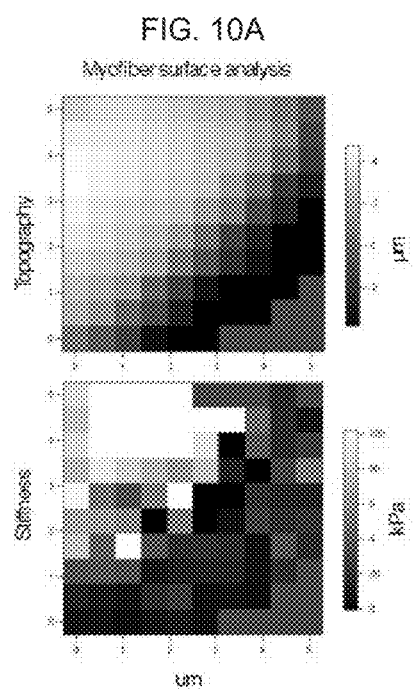
FIG. 10A-10E. Micropost-array study of the MuSC niche stiffness FIG. 10A Representative AFM surface scanning of a single myofiber explant. (Top panel) The topography of the surface (scale bar in microns) is shown. (Bottom panel) Stiffness measurements obtained with nanoindentation scanning are shown (scale bar in kPa). Freshly isolated single fibers were incubated overnight on a Laminin/Collagen-coated glass coverslip to allow them to adhere to the substrate. The following day the fibers were mounted onto the AFM stage for analysis.

We then tested the effect of the combinations of these compounds on MuSCs maintained for two days in culture (FIG. 9). Using the combinatorial Q-RT-PCR array strategy for a set of 93 genes, we found conditions in which cultured MuSCs were very similar to freshly isolated quiescent MuSCs (FIG. 1c and FIG. 9). We thus identified a defined, serum-free "quiescence medium" (QM) formulation that maintained the transcriptional signature of quiescence for at least two days in culture (FIG. 10a, b); (for formulation see FIG. 16).

Figure 1D:
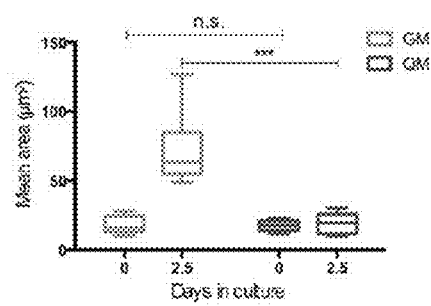
Figure 1E:
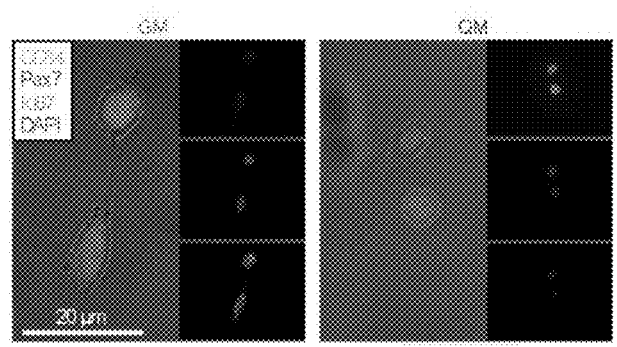

MuSCs maintained in QM had characteristics of quiescent cells. One of the most obvious changes in activated MuSCs is a dramatic increase in cell size relative to quiescent MuSCs. We found that MuSCs cultured in QM for 2.5 days remained small, similar to the size of quiescent MuSCs (FIG. 1d). Furthermore, most of the MuSCs cultured in QM continued to express the quiescent marker CD34 and did not express the cell cycle marker Ki67 (FIG. 1e). At this point we wanted to test whether quiescent MuSCs maintained in QM would retain the capacity to enter the cell cycle as a functional assessment of the state of quiescence of MuSCs maintained in QM. We observed that MuSCs cultured for 2.5 days in QM activated were able to begin proliferating when switched to growth medium (GM) (FIG. 2a). However we found that when MuSCs were cultured for one or more days beyond that, they were much less responsive to GM (FIG. 2a).

We hypothesized that when MuSCs are cultured in QM without being in their native niche (i.e. associated with a myofiber), they are not able to maintain a functional quiescent state. To test this, we cultured quiescent MuSCs still associated with myofibers and observed that they maintained their proliferative responsiveness for a longer time when cultured in QM than did cells not associated with myofibers (FIG. 2a). We conclude that the niche has a critical role in preserving a functional quiescent state of MuSCs in vitro.

Biophysical regulation of MuSC quiescence. Having found that the association of MuSCs with myofibers is able to markedly enhance a functional quiescent state maintained by QM, we surmised that an artificial niche environment in vitro might be able to substitute, at least in part, for the absence of a native niche when MuSCs have been freshly isolated by fluorescent activated cell sorting (FACS). We first sought to create an AMF that would have physical and biochemical properties of the endogenous muscle fiber and its surrounding basal lamina. Given the well-established role of the elasticity of the substrate upon which stem cells are maintained to influence cellular fate and function, we first tested the response of freshly isolated quiescent MuSCs on substrates of different elasticity by developing an in vitro system based on a micropost-array with tunable elasticity. We used microposts with elasticity ranging from 2 to 25 kPa, basing this range on the reported physiological ranges of elasticity of whole muscle and individual myofibers. We confirmed these values by performing atomic force microscopy (AFM) nanoindentation analysis on individual myofibers (FIG. 10a).

Figure 10B:
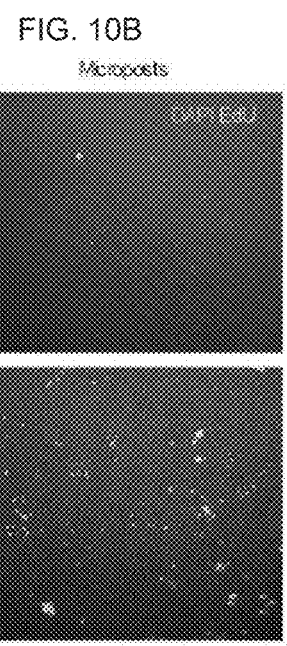
Figure 10C:
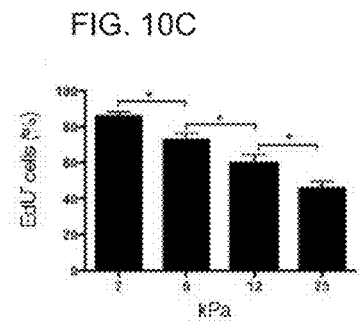
Figure 10D:
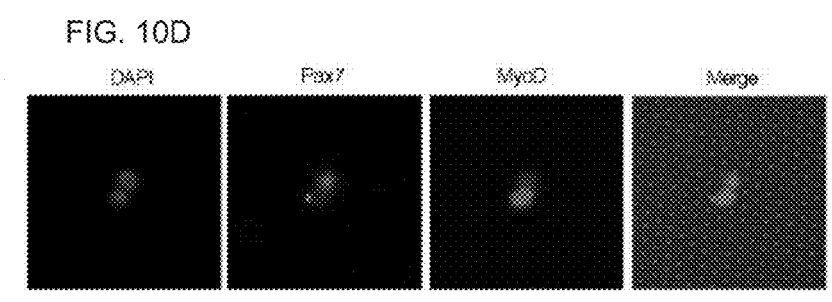
Figure 10E:
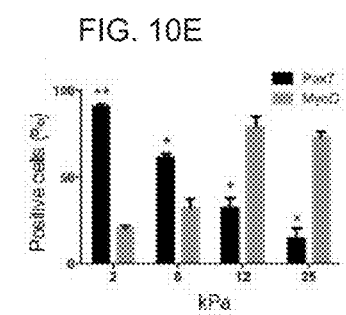

In order to determine the elasticity that is most conducive to MuSCs remaining in the quiescent state, we maintained the cells for 2 days in culture in the presence of EdU to test for DNA synthesis and entry into the cell cycle. When plated onto microposts, the propensity of the cells to remain quiescent (assessed by the absence of EdU incorporation) was directly correlated with elasticity over this range (FIG. 10b, c). Approximately 85% of the cells were quiescent at 2 kPa whereas only ~45% remained quiescent at 25 kPa. Moreover, MuSCs on the most elastic microposts were, as a population, most similar to quiescent MuSCs in terms of the percentage of cells expressing Pax7 and not expressing MyoD (FIG. 10d, e). We thus conclude that the substrate with greatest elasticity was most conducive to maintaining MuSCs in a quiescent, undifferentiated state.

Figure 11A:
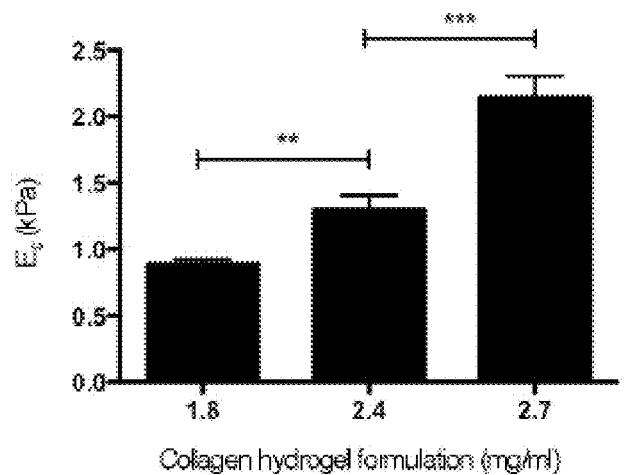
FIG. 11A-11C. Mechanical properties of Collagen-based substrates regulate MuSC properties FIG. 11A AFM nanoindentation measurements of the stiffness of Collagen-based hydrogels generated using different formulations.
Figure 11B:
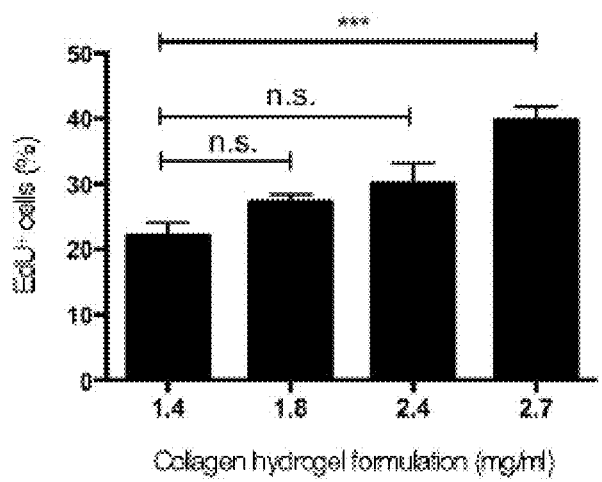
Figure 11C:
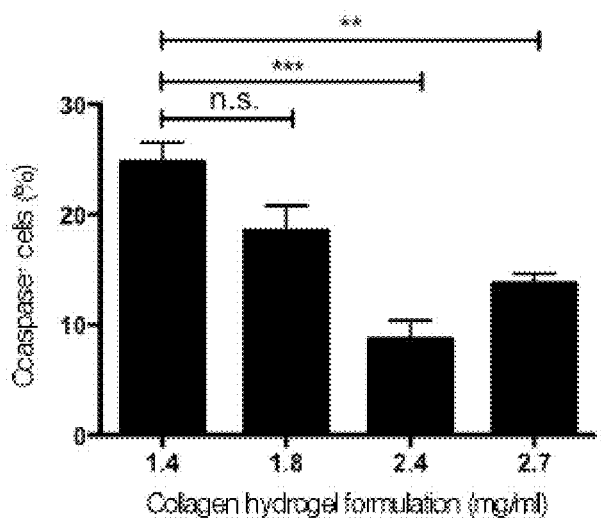

To further investigate the importance of substrate elasticity on MuSC fate and function, we used an alternate method to generate substrates of variable stiffness. As a substrate, we used the extracellular matrix (ECM) protein Collagen I, which is biodegradable, biocompatible, and easily available, and, being a lyotropic material, possesses uniquely tunable mechanical properties. In addition, collagens are components of the basal lamina which form a critical component of the MuSC niche in vivo. We generated collagen-based hydrogels with elastic moduli ranging from 0.8 to 2.5 kPa (FIG. 11a). As with micropost studies, the substrate with the greatest compliance was most effective in preventing quiescent MuSCs from entering in the cell cycle (FIG. 11b). However, intriguingly, below approximately 1.5 kPa (i.e., with a collagen hydrogel formulation at 2.4 mg/ml), the activation of apoptotic programs, as judged by active Caspase staining, increased (FIG. 11c). We thus conclude that there might be an optimal elasticity between 1 and 2 kPa, above which MuSCs tend to activate and differentiate and below which they are more prone to undergo apoptosis, and this is in accordance with a recent report showing that increased microenvironment stiffness above 2 kPa promotes myogenic cell proliferation.

Figure 2B:
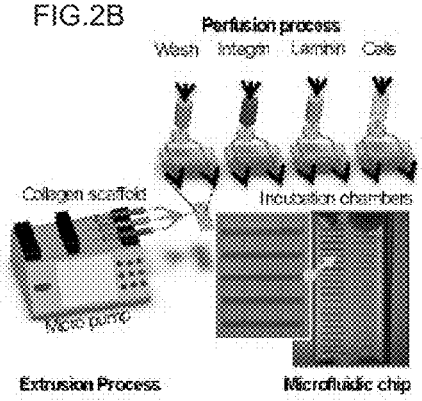
Figure 2C:
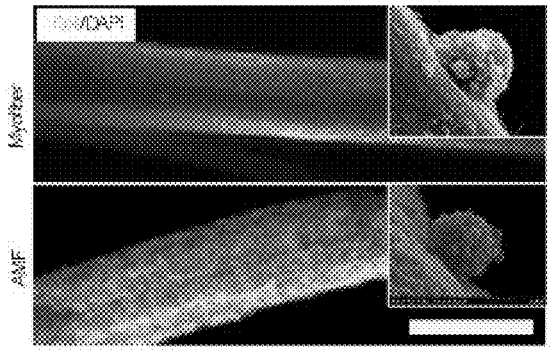
Figure 12A:
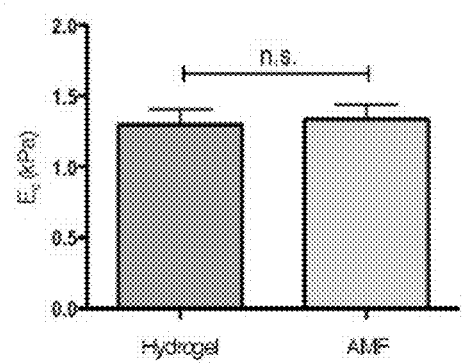
FIG. 12A-12C. Mechanical characterization of AMFs FIG. 12A AFM nanoindentation measurements of the stiffness of Collagen-based hydrogel or AMFs generated with the same formulation (error bars are s.e.m., n=3).
Figure 12B:
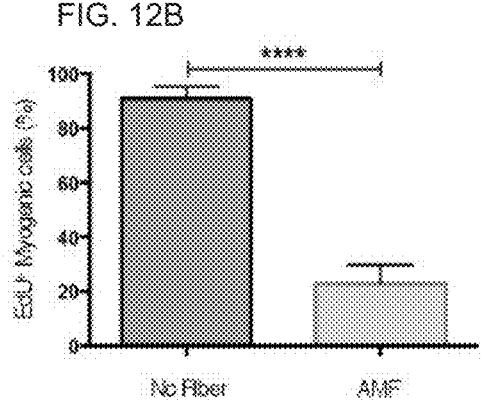
Figure 12C:
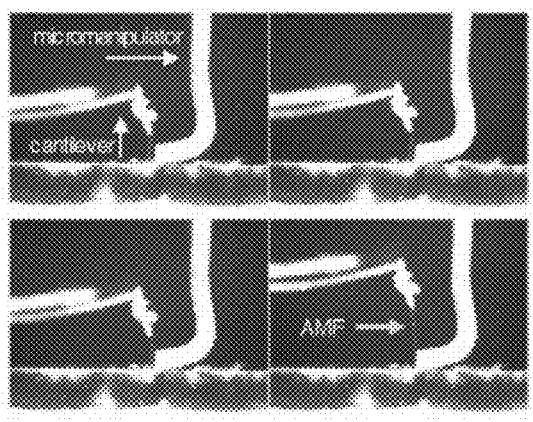
Figure 12C:
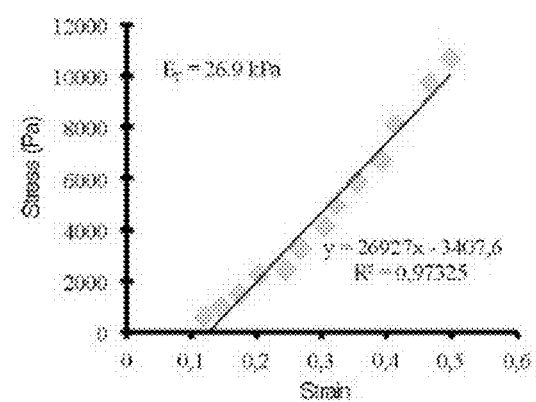

AMFs support the maintenance of MuSC quiescence. Based on these characterizations of MuSC quiescence and fate in relation to substrate elasticity and in order to mimic the quiescent MuSC niche, we developed a microfabrication process on a microfluidic chip to generate AMFs that would have the quiescence-maintaining elastic properties identified in the micropost studies (FIG. 2b). A solution of Collagen I was extruded through a nozzle using a micropump in order to generate a scaffold with parallel aligned nanofibrils, resulting from the Collagen cholesteric chemical structure 31,32,43, and with a shape and geometry similar to those of a live myofiber (FIG. 2c). These AMFs have an elasticity of 1.33±0.18 kPa (FIG. 6a), consistent with our previous measurements on Collagen I hydrogel films. When MuSCs were plated onto these AMFs (FIG. 2c), EdU incorporation was strongly reduced, consistent with the maintenance of the quiescent state (FIG. 612b). We then tested the mechanical stress capacity of AMFs to evaluate if the AMFs could maintain their structural integrity during the manipulations required for transplantation. We found a mechanical tensile modulus of approximately 27 kPa which makes them robust to manipulation in a syringe and transplantation similar to a myofiber (FIG. 12c).

MuSCs are regulated by proteins, such as the ECM protein Collagen VI, which constitute their niche. As MuSCs are closely apposed to the muscle fiber membrane in vivo, we hypothesized that muscle fiber membrane proteins might interact with MuSCs to maintain their quiescence. We found that Integrin α4β1 is expressed in the adult niche, on the muscle fiber membrane adjacent to quiescent MuSCs (FIG. 13a, b). Quiescent MuSCs express VCAM, and the primary Integrin to which VCAM binds is α4β1. We found that Integrin α4β1 was superior to other Integrin heterodimers, such as α5β1, αVβ1, and α6β1) that have been implicated in MuSC biology, in terms of reducing EdU incorporation and inhibiting cell death in vitro (FIG. 13c, d). Based on these observations, we decided to functionalize AMFs with Integrin α4β1 to provide a ligand to which the VCAM expressed on quiescent MuSCs could bind. Along the same lines, we sought to mimic other aspects of proteins that interact with quiescent MuSCs in vivo.

Figure 2D:
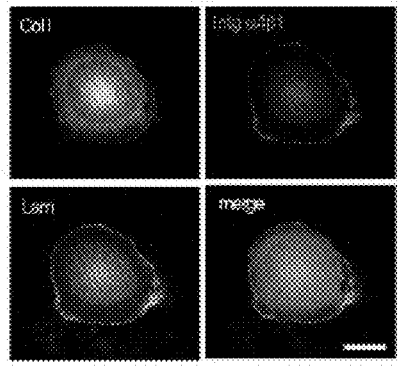
Figure 14A:
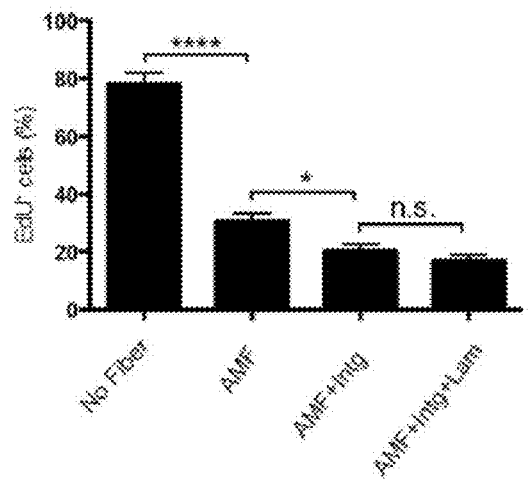
FIG. 14A-14D. Effect of functionalization of AMFs FIG. 14A Percentages of MuSCs that were $EdU_{+ve}$ on differently functionalized AMFs. MuSCs were FACS-isolated and cultured for 36 hours in the presence of EdU. The percentage of $EdU_{+ve}$ MuSCs grown in the absence of AMFs ("No Fiber") is shown for comparison (error bars are s.e.m., n=3).
Figure 14B:
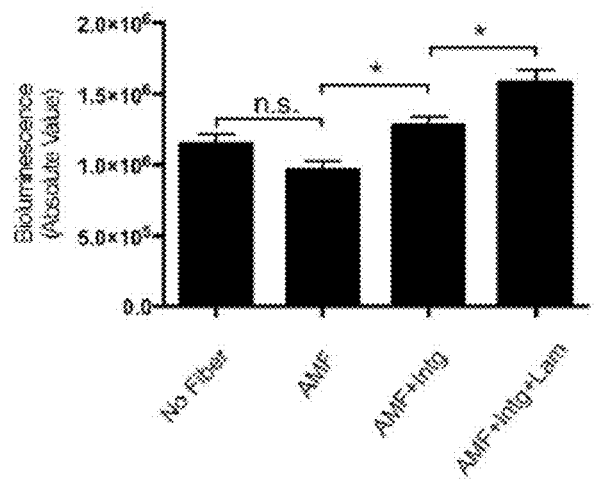
Figure 14C:
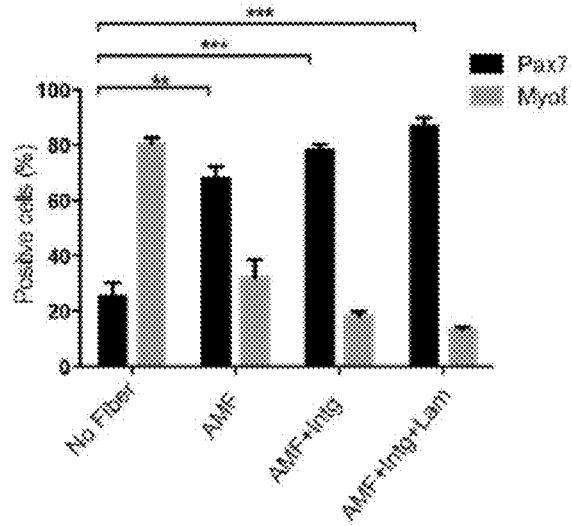

Laminins are a key component of the basal lamina surrounding MuSCs. It has been suggested that Laminins are not only structural proteins of the basal lamina but are also signaling molecules that are important for the adhesion and localization of MuSCs in their niche. We thus chose to further coat the AMF with Laminin. In order to generate functionalized AMFs, we adsorbed recombinant Integrin α4β1 followed by recombinant Laminin to the Collagen-based AMFs (FIG. 2d). When seeded onto the functionalized AMFs, MuSCs showed reduced activation as assessed by EdU incorporation, increased viability as assessed by ATP levels, and higher Pax7 and lower MyoD protein expression when compared to AMFs alone or functionalized with Integrin α4β1 only (FIG. 14a-c).

Figure 14D:
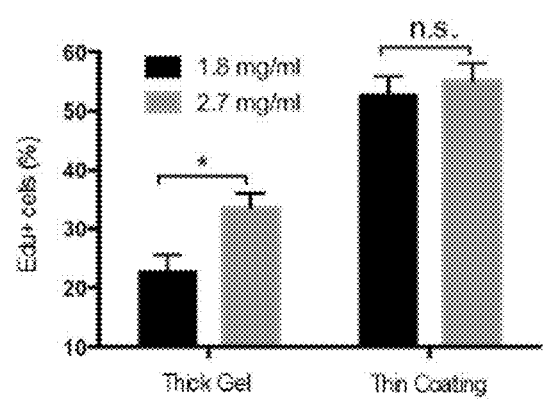

Finally, to confirm the specific role of stiffness, which is different from the role of AMF protein composition and structure, in maintaining quiescence, we compared fully functionalized AMFs generated either as thick soft gels or as thin coatings on top of a rigid substrate. We found that, consistent with previous experiments (see FIG. 11), MuSCs cultured for 36 hours on thick functionalized AMFs showed a lower degree of activation on softer substrates (FIG. 14d). However, this difference was completely lost when MuSCs were cultured on thin functionalized AMFs, a condition where the different Collagen formulations did not affect the higher stiffness of the rigid substrates to which they were attached. All of these are consistent with the functionalized AMFs promoting a viable quiescent state by virtue of their biophysical and biochemical properties.

Figure 2E:
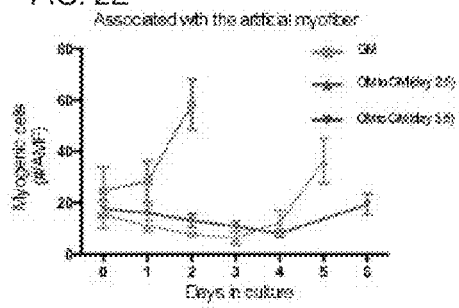

We next tested whether the MuSCs cultured on functionalized AMFs would be able to maintain reversible quiescence in QM, as we observed for MuSCs in their native niche but not for isolated MuSCs on a two-dimensional tissue culture substrate (FIG. 2e). Indeed, functionalized AMFs facilitated the maintenance of reversible MuSC quiescence. When maintained in QM for 3.5 days, quiescent MuSCs activated in response to GM with similar kinetic seen when freshly isolated MuSCs were plated in GM (FIG. 2e, f). With time, there was a gradual reduction in cell survival in QM, but even after seven days on maintenance in QM, MuSCs were able to be induced to proliferate upon exposure to GM; we did not test time points beyond this. Moreover we found that the levels of ATP showed a drastic reduction when MuSCs were not associated with a fiber but not when associated with AMFs, suggesting that the AMFs promoted a sustained viability of cultured MuSCs in QM (FIG. 2g).

We conclude that QM is able to support the survival of MuSCs in the quiescent state without inducing activation and proliferation, and that this is enhanced when MuSCs are cultured on a substrate that mimics their endogenous niche.

Preservation of the transcriptional signature of MuSC quiescence by defined culture conditions. To further characterize the state in which MuSCs persist when cultured on AMFs and in QM, we analyzed the transcriptional profile of single MuSCs under three different in vitro conditions— maintained on AMFs and in QM, maintained on two-dimensional substrate but in QM, and maintained on a two-dimensional substrate in GM and compared these to the profiles of freshly isolated quiescent MuSCs. PCA showed that MuSCs maintained in QM and on AMFs cluster with quiescent MuSCs, whereas MuSCs cultured on two-dimensional substrates do not, regardless of whether or not they are maintained in QM (FIG. 2h). In a complementary approach, we generated a cell classification model using random forests, a machine learning strategy that employs an ensemble of gene expression decision trees. In this model, we predicted cell state as either quiescent or activated based on freshly isolated MuSC transcriptional profiles (FIG. 3a). This model performed remarkably well, with 86% accuracy during cross-validation on an independent dataset (FIG. 3b, c).

Confirming the preservation of quiescence by AMFs, 45 out of 46 MuSC replicates cultured in QM on AMFs were classified as quiescent, in contrast to 8 of 33 MuSCs cultured in QM but on a two-dimensional substrate and only 4 of 22 cultured without either AMFs or QM (FIG. 3d). Analysis of the importance of the genes used to construct this predictive model revealed that the genes most discriminating between quiescence and activation were, in this order of diminishing importance, Notch2, HeyL, Notch3, MyoD, Nfat5, Eya1, Hes1, Pax7, Hey1, Ezh2, Pten, Myf5, Cd34, Atp2a2, and Foxo3 (FIG. 3e). The distribution of expression of single cell levels of these genes in quiescent MuSCs was very similar to that of MuSCs cultured in QM on AMFs, as exemplified by Pax7, Notch3 and Nfat5 (FIG. 3f).

The artificial niche enhances potency of transplanted MuSCs. In order to test whether being associated with an artificial niche would translate into greater MuSC potency in assays of transplantation, we analyzed freshly isolated MuSCs and MuSCs associated with AMFs in terms of their engraftment potential, and we compared these to MuSCs associated with native fibers as a gold standard. In each case, 100 cells were transplanted into mouse tibialis anterior (TA) muscles of immunocompromised mice that had been subjected to Cardiotoxin-induced injury 12 hours prior in order to create an environment that would promote MuSC engraftment. MuSCs were all obtained from Pax7Cre$_{ER}$/ROSA26$_{LusEAP}$ mice that had previously been treated with tamoxifen, so the donor cells expressed Luciferase and their engraftment could be assessed non-invasively. MuSCs associated with AMFs were far more potent than isolated MuSCs and nearly as potent as the same number of MuSCs associated with native fibers (FIG. 4a). These data demonstrate the importance of a niche-like environment in vitro for maintaining MuSC potency.

One of the characteristics of stem cell potency is the capacity of the cells to differentiate into new mature tissue. To assess this in MuSCs cultured in our artificial niche model, we chose to culture in QM for 2.5 days a very small number of MuSCs before transplantation. Bioluminescence signals in TAs transplanted with AMFs, similarly to myofibers, increased to a plateau. MuSCs alone were unable to engraft, likely due to the challenging conditions of transplanting only 50 cells in a non-irradiated TA muscle (FIG. 4b, c). We confirmed by immunohistochemical analysis of the same transplanted muscles that the bioluminescence signal corresponded to regenerated muscle fibers (FIG. 4d, e). Another important feature of stem cells is the capacity to self-renew. Having shown that maintenance of MuSCs on AMFs enhanced engraftment, we tested whether culture in QM and association with AMFs also increased the self-renewal potential of transplanted MuSCs, again with native fiber-associated MuSCs as controls.

As a first test of self-renewal, we examined muscles that had been transplanted with MuSCs cultured in QM (as in FIG. 4) for evidence of Luciferase-expressing cells in the satellite cell position. Indeed, we were able to detect Luciferase$^{+v}$ cells beneath the basal lamina of regenerated fibers (FIG. 5a). As a second test, we performed an injury, 40 days after the initial transplantation, on muscles previously injured and transplanted with Luciferase-expressing MuSCs. In response to this second injury, any self-renewed, transplanted MuSCs, such as those shown in FIG. 4b, would be expected to activate, proliferate and ultimately differentiate to form new muscle. Indeed, for native fiber associated MuSCs and AMF-associated MuSCs, we observed an increase of bioluminescent signal after the second injury (FIG. 5b). Cells that had been previously transplanted without any niche not only showed very little steady-state bioluminescence before the second injury, but exhibited almost no increase after it.

To further confirm that MuSCs cultured in QM for 2.5 days on AMFs retain self-renewal potential, we transplanted 1,000 quiescent MuSCs expressing the reporter fluorescence protein "enhanced YFP" (derived from a Pax7Cre$_{ER}$/ROSA26$_{eYFP}$ mouse) into a pre-injured TA muscle. After 40 days, we performed a second injury with Cardiotoxin, and 10 days later we isolated MuSCs by FACS and analyzed the number of YFP$_{+ve}$ MuSCs. TA muscles transplanted with MuSCs associated with either native fibers or AMFs showed the presence of donor-derived MuSCs (FIG. 5c). Conversely, TA muscles transplanted with MuSCs not associated with any niche structure did not have donor-derived MuSCs. We conclude that MuSCs cultured in QM and associated with AMFs, similar to MuSCs associated with native fibers, maintain quiescence in culture and retain engraftment and self-renewal potential upon transplantation.

The loss of ability of cultured MuSCs to engraft is a major challenge in developing efficient strategies to manipulate isolated stem cells for cell therapy. The optimized conditions to maintain a quiescent physiological state of MuSCs in vitro (i.e., associated with AMFs and cultured in QM) and to enhance their capacity to regenerate muscle tissue in vivo are promising for therapeutic applications. Therefore we wanted to test whether our culture conditions could preserve the transplantation potency of MuSCs after genetic manipulation in vitro. We transduced MuSCs that were either associated with AMFs and cultured in QM (our optimized conditions) or maintained on a two-dimensional substrate and cultured in GM (standard conditions) with a lentivirus expressing Luciferase and GFP. One day later, we transplanted 1,000 MuSCs from each culture into pre-injured TA muscles of immunocompromised mice. When we measured bioluminescence in vivo 30 days later, we found that MuSCs that had been maintained in our optimized conditions during lentiviral infection yielded, on average, a signal two orders of magnitude higher than MuSCs in standard conditions (FIG. 5d), showing that maintenance of a quiescent state by association with AMFs and treatment with QM could allow efficient genetic modification ex vivo without compromising MuSC potency.

Figure 6A:
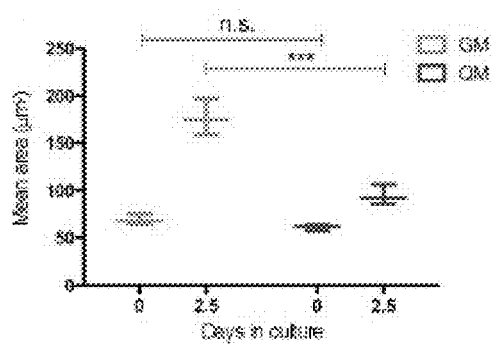
FIG. 6A-6F. QM and AMF preserve the potency of human MuSCs FIG. 6A Quantification of the areas, assessed microscopically, of hMuSCs cultured in either GM or QM immediately after isolation (0 days) or after 2.5 days in culture (n=3).
Figure 6B:
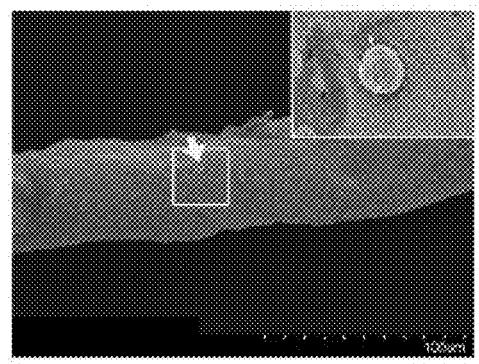
Figure 6C:
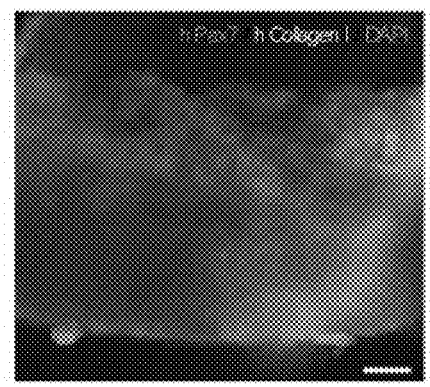
Figure 6D:
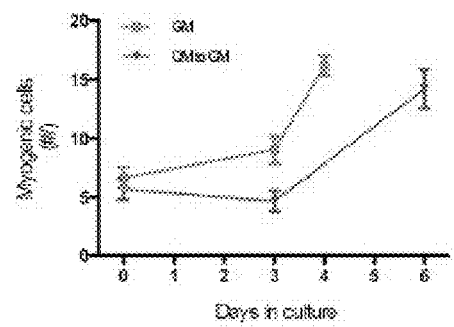
Figure 6E:
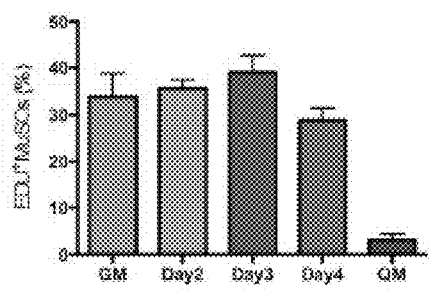

Maintenance of quiescence of human MuSCs and the enhancement of their transplantation efficacy. The capacity to maintain quiescence without a loss of potency of human MuSCs (hMuSCs) isolated from patients with genetic diseases, such as muscular dystrophies, represents an important step forward to cell therapies. In particular, this approach would allow to genetically correcting MuSCs in vitro, prior reintroducing them in the body. With this translational goal in mind, we wanted to test whether freshly isolated hMuSCs respond similarly to murine MuSCs in the experiments involving our artificial niche. First, we used FACS to isolate hMuSCs from operative samples. We then tested whether hMuSCs cultured in QM modified for human cells for 2.5 days remained small, without the dramatic change in size that occurs when they are cultured in GM. We found that, similar to murine MuSCs, hMuSCs also retain a smaller size when cultured in QM (FIG. 6a). We then generated functionalized AMFs, similar to murine AMFs but based on human proteins, and we seeded hMuSCs onto their surface in either GM or QM (FIGS. 6b and c). Using these conditions, we tested whether hMuSCs cultured on functionalized AMFs would be able to maintain reversible quiescence in QM (FIG. 6d). Indeed, functionalized AMFs facilitated the maintenance of reversible hMuSC quiescence for up to 3.5 days in QM; even at this point, the cells were able to exit quiescence and begin proliferating when cultured in GM (FIG. 6d, e).

Figure 6F:
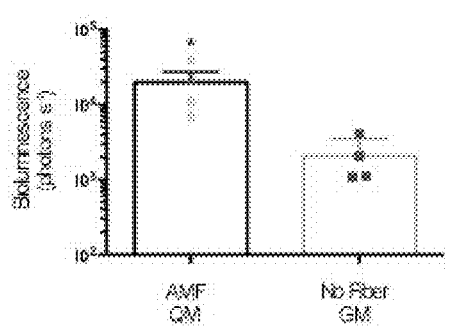

Finally, we wanted to test whether, also similar to murine MuSCs, our culture conditions could preserve the transplantation potency of hMuSCs after genetic manipulation ex vivo. Thus, we replicated the experiments previously performed with murine MuSCs (see FIG. 5d), transducing Luciferase into 1,000 hMuSCs, either cultured in our optimized conditions or in standard conditions and then transplanting them one day later into TA muscles of immunodeficient mice. When we imaged the mice non-invasively for bioluminescence 30 days later, we found that, as with the murine MuSCs, hMuSCs cultured in our optimized conditions yielded, on average, a signal one order of magnitude higher than hMuSCs cultured in standard conditions (FIG. 6f). Taken together, these results show that hMuSCs can also be isolated and genetically manipulated ex vivo in our quiescence-promoting while retaining much greater potency than hMuSCs maintained under standard conditions.

Here we provide evidence that engineering of multiparameter biomimetic microenvironments results in maintenance of not only murine but also human MuSCs in vitro that allows interventions for cell based therapeutics. Using single cell gene expression arrays and a predictive algorithm to interrogate the cell state, we analyzed individually isolated MuSCs to discover a molecular signature of quiescence. We screened molecules in a defined medium to reproduce the molecular signature of quiescent MuSCs in culture. To support in vitro quiescence, we then engineered a microscaffold that mimics biomechanical and biochemical properties of endogenous muscle fibers. Such an artificial niche is able to sustain the quiescence and potency in vitro of both mouse and human MuSCs and results in enhanced engraftment and self-renewal potential compared to traditional methods. Using this approach, we were able to overcome a major limitation of manipulating MuSCs in vitro without losing their efficacy in transplantation. Indeed, quiescent MuSCs cultured in this artificial niche were efficiently transduced with a reporter and engrafted after transplantation.

This approach not only offers new tools for studying MuSC quiescence, which is a challenge due to the fact that once removed from the niche, MuSCs quickly activate and proliferate, but also provides for stem cell therapy. Indeed, the capacity to efficiently perform gene correction in MuSCs derived from a patient with a genetic disorder, such as a muscular dystrophy, and transplant them back to repair and replace the pathogenic tissue offers great hope for improved stem cell therapeutics for muscle disorders. Moreover, the capacity to seed such MuSCs onto transplantable microscaffolds allows strategies in tissue engineering to treat traumatic injuries as in the case of volumetric muscle loss.

Materials and Methods

Animals. C57BL/6, ROSA26$_{eYFP}$, and B6.Cg-Foxn1nu/J mice were obtained from Jackson Laboratory. Pax7Cre$_{ER}$ mouse and ROSA26$_{LuSEAP}$ were provided by Dr. Charles Keller, Oregon Health and Science University, Portland, Oreg., USA. Tamoxifen injections for Cre recombinase activation were performed as described previously. To control for tamoxifen injection toxicity, we injected all mice with tamoxifen. Mice were housed and maintained in the Veterinary Medical Unit at the Veterans Affairs Palo Alto Health Care Systems. Animal protocols were approved by the Administrative Panel on Laboratory Animal Care of Stanford University.

Human skeletal muscle specimens Subjects ranged in age from 38 to 85 years. All experiments were performed using fresh muscle specimens from operative procedures. Sample processing for cell analysis began within one hour of specimen isolation. In all studies, standard deviation reflects variability in data derived from studies using true biological replicates (i.e., unique donors). Data were not correlated with donor identity.

MuSC Isolation and FACS. MuSCs were isolated as previously described. Briefly, muscles were harvested from hind limbs, dissociated to yield a fragmented muscle suspension using a gentle MACS dissociator (Miltenyl Biotec), and digested with Collagenase II (500 units per ml; Invitrogen) in Ham's F10 medium for 90 minutes. After washing, a second digestion was performed for 30 minutes with Collagenase II (100 units per ml) and Dispase (2 units per ml; Invitrogen). The resulting mononuclear cell suspension was washed, filtered and stained with VCAM biotin (clone 429; BD Bioscience), CD31-APC (clone MEC 13.3; BD Bioscience), CD45-APC (clone 30-F11; BD Bioscience) and Sca-1-Pacific-Blue (clone D7; Biolegend) antibodies at a dilution of 1:75. Streptavidin-PE-cy7 was used to amplify the VCAM signal (BD Biosciences, 1:75) and FACS grade DAPI dilactate for nonvital cell exclusion (D3571 Invitrogen). Cells isolation was performed on a BD-FACS Aria II or BD FACSAria III equipped with 488-nm, 633-nm and 405-nm lasers to obtain the MuSC population. For single cell sorting, this cell population was sorted a second time to get individual cells.

Human MuSCs were purified from fresh operative samples as previously described. Briefly, operative samples were carefully dissected from adipose and fibrotic tissue and a dissociated muscle suspension was prepared as described for mouse tissue. The resulting cell suspension was then washed, filtered and stained with anti-CD31-Alexa Fluor 488 (clone WM59; BioLegend; #303110), anti-CD45-Alexa Fluor 488 (clone H130; Invitrogen; #MHCD4520), anti-CD34-FITC (clone 581; BioLegend; #343503), anti-CD29-APC (clone TS2/16; BioLegend; #303008) and anti-NCAM-Biotin (clone HCD56; Biolegend; #318319). Unbound primary antibodies were then washed and the cells incubated for 15 min at 4° C. in streptavidin-PE/Cy7 (BioLegend) to detect NCAM biotin. The machine was carefully optimized for purity, viability, and calibration for single cell sorting. A small fraction of sorted cells was plated and stained for Pax7 and MyoD to assess the purity of the sorted population.

Single Cell Q-RT-PCR. MuSCs were FACS sorted individually into 96 well plates prepared with 9 µl RT-STA buffer (5 µl CellsDirect 2× reaction mix (Life Technologies, PN 11753-500), 0.2 µl Superscript III Platinum Taq mix, 2.7 µl nuclease free water, 0.1 µl SUPERase In RNAse inhibitor (Life Technologies) and 1 µl 1× primer mix (96×1 µl of 100 µM primer pairs plus 104 µl DNA suspension buffer)). Plates were spun down and stored at −80° C. to ensure complete cell lysis. Next, plates were thawed and subjected to a reverse transcription (RT) (15 minutes at 50° C. (RT reaction), 2 minutes at 95° C. (to inactivate reverse transcriptase and activate Taq polymerase), and subjected to a pre-amplification reaction (15 seconds at 95° C., 4 minutes at 60° C. (for 20 cycles)). Pre-amplified cDNAs were treated with Exonuclease I (2.52 µl water, 0.36 µl buffer, 0.72 µl exonuclease I (New England BioLabs, PN M0293L)) for 30 minutes at 37° C., followed by 15 minutes inactivation at 80° C. Exonuclease treated cDNAs were diluted 5× in DNA suspension buffer (TEKnova, PN T0221) and stored at −80° C. To perform the Q-RT-PCR on the Fluidigm Biomark HD, sample mixes were prepared with 2.7 µl of diluted cDNAs mixed with 3.0 µl of 2× SsoFast EvaGreen Supermix with low ROX (Bio-Rad, PN 172-5211) and 0.3 µl of 20×DNA Binding Dye Sample loading reagent (Fluidigm, PN 100-0388), vortexed and spun down. Separately, to create the assay mix, 0.3 µl of 100 µM primer mix was combined with 2.5 µl 2× Assay Loading Reagent (Fluidigm, PN 8500073) and 2.25 µl DNA suspension buffer, vortexed and spun down. A 96.96 Dynamic Array IFC (Fluidigm) was primed on an IFC Controller HX (Fluidigm). The primed Dynamic Array was loaded with the assay and sample mixes using an IFC Controller HX. Finally the PCR was performed on a Biomark HD, using protocol GE 96×96 PCR+Melt v2 (2400 seconds at 70° C., 30 seconds at 60° C., 60 seconds at 95° C. hot start, 30 cycles (5 seconds at 95° C., 20 seconds at 60° C.), followed by a melt curve). Biomark data was analyzed using Q-RT-PCR Analysis software (Fluidigm). Data were exported into Microsoft Excel for further analysis. For each amplicon, a limit of detection (LOD) was determined by running 10-fold serial dilutions of embryonic cDNA in 6 replicates. Limit of detection was set to the lowest dilution for which all six replicates give a PCR signal. This value was set to denote the amplification of 2-10 copies of transcript per reaction chamber. A list of primers in FIG. 16.

Single Cell Data Analysis and Molecular Signature. Raw Ct values were filtered and normalized according to the manufacturer's instructions and are represented in FIG. 16. Log2 (expression values) were used for all analyses. For analyses involving multiple experiments (random forests and violin plots), only genes with primers common to all experiments were used, and datasets were first batch-corrected using COMBAT. For PCA, genes were mean-centered and unit variance-scaled. Kmedians clustering with k-means$_{++}$ seeding using Manhattan distance was performed for genes, using $k=2^{64}$. Random forest construction was done using 8000 trees and 25 genes with 5 random genes selected at each node. Conditional variable importance for the genes involved in random forest construction was calculated as the mean decrease in out-of-bag (OOB) accuracy of the trees after permuting that gene within sample subsets split by correlated genes with an association p<0.2. P-values for these conditional variable importance measures are based on 1000 permutations of the response variable to mimic the distribution of variable importance when no gene has predictive value. Hierarchical clustering used Manhattan distance and complete linkage after mean-centering and UV-scaling genes. P-values are approximately unbiased values calculated using multiscale bootstrap resampling with 10,000 resamples at ten sizes. Scripts generated in R computational language to analyze the data are posted. Topological data analysis (TDA) methods were used to identify the quiescent population signature in an unsupervised fashion using the Ayasdi Iris software (Ayasdi Inc., Menlo Park Calif.). TDA benefits from properties inherent in the classic topological methods useful for characterizing shape, as applied to point cloud space. These properties include deformation invariance in the form of relative noise insensitivity; compressed representation, as reified by the partitioning and clustering steps; and coordinate freeness that relies only on the notion of similarity between points.

While mathematical details regarding the method of construction for the topological network is described in complete form elsewhere, we summarize the approach here briefly. Two key parameters are needed for generating a topological analysis: a notion of similarity, or metric, and filter(s). For each point X, in this case a single cell, a filter function $f$ is applied yielding some real-valued output Y. Based on the value of Y for each X, the points are binned with some overlap, the span of which is variable. Then, for each X and for all bins, a metric is used to determine the distance d(X,X') in the original space. A partial clustering scheme is finally used to aggregate points within bins and form connections between points across multiple bins. In the topological network, the aggregated points form the nodes (and thus collections of points), while the edges appear when two aggregations in the clustering contain one or more of the same points. The method described above essentially generates Reeb graphs from the data, the result of which can be used for identification of natural segmentations of points for noisy data, and has been useful in identifying patterns in complex, high-dimensional datasets. In the present case, the data is based on population signatures across 35 genes over the single cells. For this dataset, the metric used was correlation, and the functions applied were principal and secondary components (metric embedded). The resulting representation revealed a distinct segregation of the quiescent population. A non-parametric statistical test (Kolmogorov-Smirnov) was used to identify the most significant markers for the quiescent population relative to the entire dataset.

Single-fiber Explants. Extensor digitorum longus (EDL) or flexor digitorum *brevis* (FDB) muscles were excised and digested in Collagenase II (500 units per ml in Ham's F10 medium) as previously described. Fibers were then washed extensively and cultured in medium containing Ham's F10, 10% horse serum and 0.05% chick embryo extract. Every 24 hours, 50% of the medium was replaced with Ham's F10 medium with 20% fetal bovine serum (FBS). EDL fibers were cultured in suspension. Fixed fibers were stained and the number of MuSCs was quantified per fiber.

Micropost-arrays. Elastomeric micropost-arrays were generated with PDMS by replica-molding as published elsewhere 76. Briefly, PDMS prepolymer was poured over a template containing an array of holes, degassed under vacuum, cured at 110° C. for 20 hours and peeled off the template. Microposts were fabricated 1 μm in diameter and 3 μm of center-to-center distance; elasticity of the microposts was changed by modulating the amount of cross-linker and their length 38 to obtain nominal spring constants of 1.9223 nN/μm, 7.22106 nN/μm, 18.1905 nN/μm, 32.0312 nN/μm for effective moduli of approximately 2, 6, 12, 25 kPa respectively.

Injections. Mice were anaesthetized using isoflurane through a nose cone. Muscle injury was induced by injecting 20 μl of Cardiotoxin (Invitrogen) into TA muscles.

Transduction. Luciferase and GFP protein reporters were subcloned into a third generation HIV-1 lentiviral vector and used to transduce freshly isolated MuSCs.

Histology and Immunohistochemistry. For hematoxylin and eosin staining, TA muscles were dissected and directly frozen in OCT (Tissue-Tek). For immunohistochemistry, TA muscles were fixed for 5 hours using 0.5% electron microscopy-grade paraformaidehyde and subsequently transferred to 20% sucrose overnight. Muscles were then frozen in OCT, cryosectioned at a thickness of 6 μm and stained using an M.O.M. kit (Vectorlabs) or a Zenon labelling kit (Invitrogen) according to the manufacturers' instructions.

Atomic Force Microscopy. AFM was used to analyze Collagen-based hydrogel properties. Gels were made from bovine tendon Collagen I (Cellmatrix I-A, Nitta Gelatin, Osaka, Japan). The Collagen concentrations that were tested ranged from 1.8 to 2.7 mg/ml. Varying Collagen concentrations were achieved by reducing the volume of Collagen stock solution (3.0 mg/ml) and replacing that volume with an equivalent amount of 10× Ham's F12 media (Life Technologies, Carlsbad, Calif.) without sodium bicarbonate. Reconstitution buffer volumes were kept constant across all conditions (FIG. 16). Reconstitution buffer was comprised of 2.2 g $NaHCO_3$(Sigma-Aldrich, St. Louis, Mo.) in 100 ml of 0.05N NaOH and 200 mM HEPES. Concentration [mg/ml] Collagen stock [μl] Ham's F12 [μl] Reconstitution buffer [μl] Collagen:media:buffer ratio 2.7 450 0 50 9:0:1 2.4 400 50 50 8:1:1 1.8 400 150 50 6:3:1 FIG. 16 Collagen matrix compositions utilized to generate encapsulating matrices. Gel films were generated according to protocol and kept on ice prior to casting onto glass surfaces for testing. Samples were given 30 minutes to gel at 37° C. and then rehydrated with phosphate buffer solution (PBS, Life Technologies, Carlsbad, Calif.) for a minimum of 15 minutes prior to testing. Similarly, individual muscle fibers were adhered to glass surfaces prior to testing and submerged in PBS. Gel and muscle fiber samples were tested while remaining submerged in PBS. Short silicon contact mode probes (SHOCON, Applied NanoStructures. Mountain View, Calif.) were used to collect individual force measurements from all samples. Probes were rinsed with FBS (Life Technologies, Carlsbad, Calif.) prior to testing to prevent non-specific adsorption of samples to the probe tip. Force measurements were collected using 1 μm force distances and 1 Hz scanning rates with a 0.5 V trigger point upon contact. The integral gain was set to 10 due to the submerged testing conditions. A Hertz indentation model for cone tip geometry was used to fit the data. Poisson ratios of 0.4 and 0.33 were assumed for Collagen gels and primary tissue, respectively. All AFM data were collected using an Asylum Research MFP-3D-BIO.

AMF Tensile Testing Analysis. Collagen fibers were extruded according to protocol and transferred to 1.5 ml Eppendorf tubes filled with PBS. Eppendorf tubes were rinsed once with FBS prior to use to prevent non-specific adsorption of fibers to the tube walls. Tubes were then sealed, placed on ice, and transferred to the CellScale Biomaterials Testing facility. All tensile testing was performed on-site at the CellScale facility using the Microsquisher device. AMF samples were tested in a hydrated state. One end of the AMF fiber was fixed in place and the other was attached to the moving force transducer wire of the Microsquisher device. This enabled collection of mechanical data in a tensile rather than compressive mode. Force versus displacement curves were then converted to stress versus strain curves for calculation of the Young's moduli.

Master Mold Fabrication. All photo masks were designed using SolidWorks (Solidworks Corp. Waltham, Mass.) and printed at a resolution of 20,000 dots per inch on a transparency film (CAD/Art Services). Master Mold fabrication was performed as described elsewhere[77]. Briefly, the flow-layer master was fabricated from a combination of positive and negative photoresists using a three-step lithography process. Channel sections were fabricated from the resist material SU8-2010. SU8 2010 (MicroChem, Newton, Mass.) was spun onto a silicon wafer (3,000 rpm for 45 seconds), baked before exposure (1 minute at 65° C., then 3 minutes at 95° C.), exposed through a negative transparency mask (40 seconds at 7 mW/cm2), baked after exposure (1 minute at 65° C., then 3 minutes at 95° C.), and developed in an SU8 nanodeveloper (MicroChem). Channel sections were fabricated using the positive photoresist SJR 5740 (MicroChem). To promote photoresist adhesion, the wafer was first treated with hexamethyldisilazane (Microprime HP-Primer; ShinEtsu MicroSi, Phoenix) (1 minute at 1 atmosphere). The photoresist was spun onto the patterned wafer (2,000 rpm for 60 seconds), soft baked (1 minute 45 seconds at 95° C.), aligned to the existing features, exposed (45 seconds at 7 mW/cm2), and developed (20% Microposit 2401 developer; MicroChem). The mold was then annealed (20 minutes at 120° C.), and hard baked (2 hours at 170° C.). Low-impedance input and output channels were fabricated to allow for the rapid flushing of viscous reagents. A 60 mm layer of SU8 2075 (MicroChem) was spun onto a silicon wafer (3,000 rpm for 60 seconds), baked before exposure (7 minutes at 65° C., then 20 minutes at 95° C.), aligned to the primary flow structure, and exposed through a negative transparency mask (40 seconds at 7 mW/cm2), baked after exposure (1 minute at 65° C., then 15 minutes at 95° C.), and developed in an SU8 nanodeveloper (MicroChem). Control features (25 mm high) were fabricated on a separate wafer using a single lithographic step. SU8 2025 (MicroChem) was spun onto a silicon wafer (3,000 rpm for 45 seconds), baked before exposure (1 minute at 65° C., then 3 minutes at 95° C.), aligned to the primary flow structure, exposed through a negative transparency mask (40 seconds at 7 mW/cm2), baked after exposure (1 minute at 65° C., then 3 minutes at 95° C.), and developed in an SU8 nanodeveloper (MicroChem).

Microfluidic Device Fabrication. The microfluidic chip was fabricated as previously described. Briefly, using silicone elastomer (General Electric RTV 615) the technique of multilayer soft lithography was applied. To facilitate the release of the elastomer from the mold, all molds were treated with chlorotrimethylsilane (Aldrich). Liquid silicone elastomer (20 parts A:1 part B) was spun onto the control master (2.400 rpm for 60 seconds) and baked in a convection oven at 80° C. for 60 minutes. Liquid silicone elastomer (5 parts A:1 part B) was poured on the flow master to a thickness of 7 mm, degassed, and baked at 80° C. for 75 minutes. The bonded elastomer was then peeled from the control mold, and access ports were punched at the flow and control inlets using a 0.055-inch punch (Technical Innovations, Gaithersburg, Md.). The device was peeled from the silicon wafer, cut to size, and sealed to a glass substrate for mechanical rigidity via plasma bonding. The final design, sized to fit a standard 22×50 mm glass coverslip, consisted of two rows of twenty culture chambers (500 µm×300 µm×7 mm) each, with media inlet and outlet ports and smaller (50 µm×50 µm) flow channels connecting the culture chambers of each row. This design was chosen because it allows for the side-by-side comparison of two different culture conditions on the same chip, thus eliminating any undesired variability in handling or manipulation between experimental conditions while maintaining identical conditions within experimental groups. The photomasks, master mold and polydimethylsiloxane (PDMS) chips were fabricated at the Stanford Microfluidics Foundry based using multilayer soft lithography. After that, 18G needles were cut down to approximately 1.5 cm and inserted into the inlet and outlet ports where they were secured with additional PDMS. Tygon tubing (1/16") was used to connect the inlet needles to a SP2201 syringe pump (World Precision Instruments; Sarasota, Fla.), which was used to control all subsequent fluid manipulations within the device.

Artificial Muscle Fiber Fabrication. The Collagen used was bovine tendon Collagen I (Nitta Gelatin, Japan) or Collagen solution from human fibroblasts (Sigma-Aldrich, USA). All polymerization procedures were carried out using sterile techniques and sterile solutions. Polymerization was achieved by mixing monomeric Collagen solution, F10 medium, and reconstitution buffer at a ratio of 8:1:1, according to manufacturer's instructions. Lower modulus Collagen was achieved by decreasing the amount of Collagen solution and replacing that volume with F10 medium. All solutions and mixtures were kept on ice to slow down polymerization. Collagen fibers were then produced by extruding through a 26S fine-gauge syringe needle (Hamilton Company; Reno, Nev.) with an internal needle diameter of 0.127 mm. The syringe plunger was pushed at a constant rate of 5 µl/min by a SP2201 syringe pump (World Precision Instruments; Sarasota, Fla.), volume setting to 10 µl and inner syringe diameter to 0.461 mm. All Collagen fibers were extruded into warm PBS in petri dishes or through the PDMS in microchambers. The chip chambers were pre-coated with 10% horse serum for 10 minutes and rinsed twice with PBS prior to storing the Collagen fibers. The coating step was performed to prevent non-specific adhesion of Collagen fibers to the chambers. For functionalizing the Collagen microfibers, mouse or human recombinant Integrin α4β1 was perfused in the chip and absorbed on the surface of the Collagen fiber by incubating for 1 hour. The scaffold was then washed by perfusing with PBS for 30 minutes. A third functionalization step was performed by perfusing mouse or human Laminin and incubating for 1 hour. A washing step was performed by perfusing with PBS for 1 hour. FACS sorted mouse or human MuSCs were then perfused in the chamber, allowed to adhere to the scaffold, cultured in the chip until fixed with 1% PFA and removed for analysis or employed unfixed for transplantation. Cell density in the media perfused was titrated in order to obtain an average number of 10±5 to 100±20 (according to the experiment) MuSCs per AMF.

Transplantation. Recipient nude mice were pre-injured with Cardiotoxin under anesthesia 12 hours before transplantation. Mice received randomly via intramuscular injection 50 to 1000 MuSCs either in suspension, associated with viable muscle fibers, or associated with AMFs. Live MuSCs (expressing YFP, GFP or immunostained) were counted at a fluorescent microscope prior to transplantation. The injection was performed with a pulled transparent glass needle pre-coated with FBS, that was connected with silicon tubing, pre-loaded with mineral oil, to a Hamilton syringe. The syringe was controlled by an automated micropump (SP2201 syringe pump, World Precision Instruments; Sarasota, Fla.). Cell suspension or individual fibers were carefully loaded in the needle under a microscope. A small opening of the skin was performed to expose the TA muscles. The needle was inserted into the proximal TA muscle and the cells or fibers were slowly injected into the muscle. The needle was left undisturbed for 5 minutes in the muscle. Before extracting the needle, the injection site was sealed with surgical glue (Tiessel, fibrin sealant, Baxter) to prevent leaking of cells or fibers. The skin wound was carefully sutured with one point stitch (Coated Vicryl suture, 8-0, Ethicon).

Bioluminescence Imaging. Bioluminescent imaging was performed using the Xenogen IVIS-Spectrum System (Caliper Life Sciences). Mice were anesthetized using 2% isoflurane and 100% oxygen at a flow rate of 2.5 V min. Then 300 µl of 50 mg/ml sterile D-Luciferin (Biosynth International Inc.) dissolved in PBS was administered by intraperitoneal injection. After 23 minutes from the substrate injection, the mice were imaged for 30 seconds at the maximal light collection (f-stop 1) at the highest resolution (small binning). Each image was saved for subsequent analysis. Imaging was performed in bind: the investigators performing the imaging did not know the identity of the experimental conditions for the transplanted cells.

Bioluminescence Image Analysis. Analysis of each image was performed using Living Image Software, version 4.0 (Caliper Life Sciences). Briefly, a manually generated circle was placed on top of the region of interest and resized to completely surround the limb or the specified region on the recipient mouse. Imaging was performed in bind: the investigators performing the analysis did not know the identity of the experimental groups.

Bioluminescence Analysis of ATP levels. ATP levels were measured using the CellTiter-Glo (Promega) luminescent assay as described by the manufacturer.

Scanning Electron Microscopy. Single myofibers or AMFs were fixed (4% PFA and 2% glutaraldehyde in 0.1M NaCacodylate buffer, pH 7.3) at 4° C., post-fixed in 1% OsO$_4$, and transferred to microporous (120 µm) cylindrical capsules (Electron Microscopy Sciences, Hatfield, Pa.) for gradual dehydration in ethanol, followed by critical point drying (Tousimis, Rockville, Md.). Samples were then mounted onto aluminum stubs, Au/Pd sputter-coated and imaged with a Zeiss Sigma FESEM (Thornwood, N.Y.) operated at 2-5 kV with SE detection. Hydrated samples were similarly fixed and then mounted fully hydrated onto the chamber in a Coolstage (Deben, UK) for imaging with a Hitachi 3400N Variable Pressure (VP) SEM (Hitachi Northridge, Calif.) operated at 15 kV and 50 Pa using BSE detection in VP-mode.

Recombinant Proteins. The recombinant proteins used in this study were, for mouse: Integrin α4β1 (R&D cat 7810-A6-050); Integrin α5β1 (R&D cat 7728-A5-050); Integrin αVβ1 (R&D cat 7705-AV-050); Integrin α6β1 (R&D cat 7810-A6-050); TGFβ1 (R&D Systems cat 7666-MB-005); Laminin (Invitrogen cat 23017-015). For human: Integrin α4β1 (R&D cat 5668-A4-050); Laminin (BioLamina cat LN-211); Collagen (Sigma-Aldrich cat C2249).

Immunofluorescence. Immunofluorescence was performed using a Zeiss Observer Z1 fluorescent microscope (Zeiss) equipped with a Hamamatsu Orca-ER camera or a Zeiss confocal system LSM710 (Zeiss). Data acquisition and fiber-diameter measurements were performed using Improvision Volocity software (Perkin Elmer) or Zeiss LSM ZEN software (Zeiss).

Antibodies and Staining. Antibodies used in this study were to the following proteins, with the source of each antibody indicated: Pax7 (DSHB); Ki67 (Abcam 15580 and BD 558615); CD34 (Biolegend 343501 and Biolegend 119213); Laminin (Sigma L9393, Millipore MAB1903 and One World Lab C13071); cleaved Caspase3 (Cell Signaling 9669); MyoD (Dako M3512; Santa Cruz sc-760); green fluorescent protein (GFP) (Invitrogen A11122 and Abcam ab13970); Collagen I (Cedarlane clone 50151AP); Integrin α4β1 (ABcam ab8991-100 and ABcam ab24695). EdU chemical staining was performed as indicated by the manufacturer (Invitrogen).

Statistical Analysis. Unless otherwise noted, all statistical analyses were performed using GraphPad Prism 5 (GraphPad Software). All error bars represent s.e.m.; * $P<0.05$; * $P<0.001$;  $P<0.0001$;  $P<0.00001$.

Sample size. A minimal number of animals necessary to obtain statistically relevant experimental data was predicted and utilized. The size of groups needed was determined based on previous studies or preliminary data. The number needed per group was estimated based on expected magnitude of any measurable outcome to achieve statistical significance, and was based to achieve a power to 80% and P value of <0.054. The coefficient of variation ranges from <5% to approximately 30%. To detect difference of 20% with a 10% standard deviation (SD) (using the bioluminescence assays as the limiting assay, to calculate the highest variability), 4 mice per group was calculated to be required (2 TA muscles per mouse); with a 20% SD of the assay, 13 (26 muscle) mice per group; with a 30% SD of the assay, 20 mice (40 muscles). Thus, based on the variation used in our previous work, it was expected that 4-13 mice with each group was required.

General Methods. Unless stated otherwise, sample size (n values) are reported as biological replicates of mice and/or SC isolations from separate mice performed on 28 different days. In most cases, the data presented were compiled over the course of 3 years, as mice with the appropriate genotype became available. Therefore the magnitude of the effect and variability in the measurements were primary factors in determining sample size and replication of data. Although samples were not explicitly randomized or blinded, mouse identification numbers were used as sample identifiers and thus the genotypes and experimental conditions of each mouse/sample were not readily known or available to the experimenters during sample processing and data collection. The only criteria used to exclude samples involved the health of the animals, such as visible wounds from fighting. In these cases, the animals were handled in accordance with approved IAUCUC guidelines.

Study Approval. Animals were handled and housed according to the guidelines set forth by the Veterinary Medical Unit of the VA Palo Alto Health Care System, and all procedures were approved by the IACUC prior to being performed. For human subjects, all operative specimens were obtained with appropriate written informed consent according to a protocol approved by the Stanford University Institutional Review Board.

Example 2

Induced Quiescence of Expanded Muscle Stem Cells

Quiescent Media (QM) is a defined condition to culture murine and human muscle stem cells (MuSCs) isolated from their microenvironment, or niche, where they reside in a quiescent state. QM maintains MuSCs in a quiescent state in vitro in an artificial environment that mimics the endogenous niche (also called "artificial niche"). This quiescence state results in enhanced stem cell potency once the cells are reintroduced in the body (shown in Example 1).

Another application of QM is to induce a quiescent state-like state to proliferating myogenic progenitors derived from MuSCs called myoblasts (MBs), to enhance their potency for cell therapy, such as in transplantation assays.

Figure 15A:
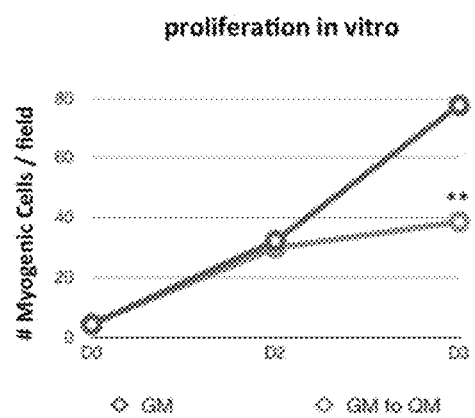
FIG. 15A-15C. Induction of quiescence in muscle blast cells.
Figure 15B:
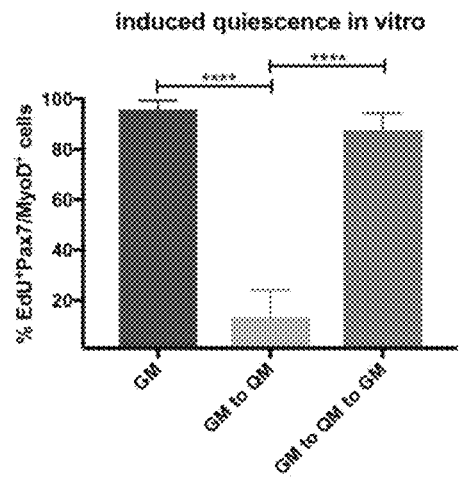

To test this, we asked whether MBs cultured in QM can be reverted to a quiescent state-like similar to MuSCs. First, we isolated MuSCs by fluorescent activated cell sorting from a donor mouse. We then cultured and expanded them in a serum rich growth media (GM). After two weeks in culture, we switched GM to QM in the presence of EdU, an analog of DNA that is incorporated into the cells during the cell cycle. Subsequently, we fixed the cells after 24 hours and stained them for EdU. We found that MBs cultured in QM stopped proliferating (FIG. 15A). Moreover, MBs cultured in QM stained negative for EdU, suggesting an arrested cell cycle (FIG. 15B). A functional quiescent state of MuSCs must be reversible. Indeed, when MBs cultured in QM where switched back to GM, stained positive for EdU, suggesting that they re-entered into the cell cycle (FIG. 15B).

Freshly isolated quiescent MuSCs are far more efficient cells compared to cultured MBs when employed in cell transplantation assays. In particular, MuSCs are the gold standard in cell therapy, such as in developing therapeutic applications for muscular dystrophies (Montarras, Science 309, 2064-2067 (2005)). However, the small number of MuSCs that can be isolated from a patient limits their use in the clinical setting. Our artificial niche showed that even a small number of MuSCs maintained in a quiescent state while genetically manipulated in vitro before being transplanted results in greater engraftment and self-renewal potency when compared to MBs (shown in Example 1).

However, the capacity of expanding MuSCs in vitro first, and then reprograming them to reacquire a potent state prior transplantation greatly improves applications and designs of cell therapies. To test this, we isolated MuSCs from a donor mouse expressing the bioluminescent protein Luciferase (Luc). We cultured these $Luc_+$ MuSCs in GM for two weeks, expanding them in proliferating $Luc_+$ MBs (from 50,000 MuSCs to 1,000,000 MBs). Next, we switched 500,000 $Luc_+$ MBs from GM to QM, where we cultured them for 24 hours. In parallel we maintained 500,000 MBs in GM for the same amount of time. We then transplanted these cells in immunodeficient NOD-SCID recipient mice. We transplanted these cells into tibialis anterior muscles that have been pre-injured with cardiotoxin, a procedure employed to facilitate the engraftment of transplanted cells. In particular, 500,000 $Luc_+$ MBs cultured only in GM were transplanted in the left legs, and 500,000 $Luc_+$ MBs cultured in GM and switched in QM for 24 hours were transplanted in the right legs.

Figure 15C:
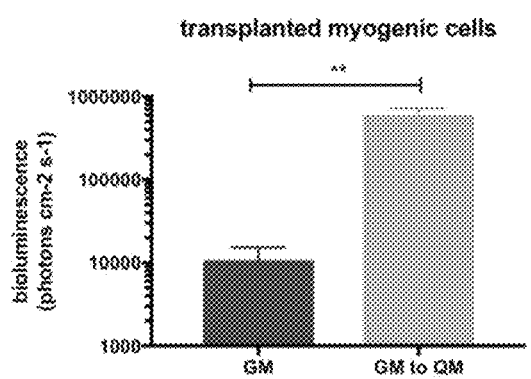

After two weeks, we imaged non-invasively the bioluminescence signals in these mice. We found that cultured MBs that were switched to QM from GM resulted in a bioluminescent signals 1.5 order of magnitude higher than MBs cultured in GM only. These results suggest an improved potency of myogenic proliferating cells cultured in QM in our artificial niche (FIG. 15C).

What is claimed is:

1. A composition, comprising:
   four or more components selected from the group consisting of elcatonin, forskolin, insulin-transferrin-selenium, SB203580, SU5402, TGFβ, and a serum replacement.

2. The composition of claim 1, further comprising a substrate.

3. The composition of claim 2, wherein the substrate has an elasticity of between about 0.01 kPa to 2000 kPa.

4. The composition of claim 2, wherein the substrate is a polymeric substrate.

5. The composition of claim 4, wherein the polymeric substrate is a biological polymer.

6. The composition of claim 2, further comprising a biomolecule, wherein the biomolecule is linked to the substrate.

7. The composition of claim 1, wherein the composition further comprises fibronectin, laminin, or collagen.

8. The composition of claim 1, wherein the composition is serum-free.

9. The composition of claim 1, wherein the composition comprises five or more components selected from the group consisting of elcatonin, forskolin, insulin-transferrin-selenium, SB203580, SU5402, TGFβ, and a serum replacement.

10. A composition, comprising:
    four or more components selected from the group consisting of elcatonin, forskolin, insulin-transferrin-selenium, MGCD-265, JNJ-7706621, SB203580, SU5402, somatostatin, TGFβ, and a serum replacement.

11. The composition of claim 10, further comprising one or more of MGCD-265, JNJ-7706621 and somatostatin.

12. The composition of claim 11, further comprising a substrate.

13. The composition of claim 12, wherein the substrate has an elasticity of between about 0.01 kPa to 2000 kPa.

14. The composition of claim 12, wherein the substrate is a polymeric substrate.

15. The composition of claim 14, wherein the polymeric substrate is a biological polymer.

16. The composition of claim 11, wherein the composition is serum-free.

17. The composition of claim 11, wherein the composition comprises five or more components selected from the group consisting of elcatonin, forskolin, insulin-transferrin-selenium, MGCD-265, JNJ-7706621, SB203580, SU5402, somatostatin, TGFβ, and a serum replacement.

18. The composition of claim 11, wherein the composition comprises six or more components selected from the group consisting of elcatonin, forskolin, insulin-transferrin-selenium, MGCD-265, JNJ-7706621, SB203580, SU5402, somatostatin, TGFβ, and a serum replacement.

19. A composition, comprising:
    an isolated population of stem cells in a culture medium, the culture medium comprising four or more components selected from the group consisting of elcatonin, forskolin, insulin-transferrin-selenium, SB203580, SU5402, TGFβ, and a serum replacement.

* * * * *